(12) United States Patent
Kaplan et al.

(10) Patent No.: US 8,996,133 B2
(45) Date of Patent: Mar. 31, 2015

(54) METHODS AND APPARATUS FOR LEAD PLACEMENT ON A SURFACE OF THE HEART

(75) Inventors: Aaron V. Kaplan, Los Altos, CA (US); Kevin F. Hahnen, Duluth, GA (US)

(73) Assignee: SentreHEART, Inc., Redwood City, CA (US)

( * ) Notice: Subject to any disclaimer, the term of this patent is extended or adjusted under 35 U.S.C. 154(b) by 109 days.

(21) Appl. No.: 11/742,165

(22) Filed: Apr. 30, 2007

(65) Prior Publication Data

US 2007/0203554 A1 Aug. 30, 2007

Related U.S. Application Data

(62) Division of application No. 10/144,205, filed on May 10, 2002, now Pat. No. 7,610,104.

(51) Int. Cl.
*A61N 1/05* (2006.01)
(52) U.S. Cl.
CPC ....... *A61N 1/0587* (2013.01); *A61N 2001/0578* (2013.01)
USPC ........................................... 607/122; 607/129
(58) Field of Classification Search
USPC ........................... 607/115, 122, 129; 606/129
See application file for complete search history.

(56) References Cited

U.S. PATENT DOCUMENTS

| | | |
|---|---|---|
| 3,496,932 A | 2/1970 | Prisk et al. |
| 3,703,169 A | 11/1972 | Ouchi |
| 3,896,793 A | 7/1975 | Mitsui et al. |
| 4,030,509 A | 6/1977 | Heilman et al. |
| 4,181,123 A | 1/1980 | Crosby |
| 4,257,278 A | 3/1981 | Papadofrangakis et al. |
| 4,280,510 A | 7/1981 | O'Neill |
| 4,319,562 A | 3/1982 | Crosby |
| 4,424,818 A | 1/1984 | Doring et al. |
| 4,662,377 A | 5/1987 | Heilman et al. |
| 4,706,655 A | 11/1987 | Krauter |
| 4,759,348 A | 7/1988 | Cawood |
| 4,765,341 A | 8/1988 | Mower et al. |
| 4,817,608 A | 4/1989 | Shapland et al. |
| 4,841,949 A | 6/1989 | Shimizu et al. |
| 4,887,606 A | 12/1989 | Yock et al. |
| 4,944,753 A | 7/1990 | Burgess et al. |
| 4,991,578 A | 2/1991 | Cohen |

(Continued)

FOREIGN PATENT DOCUMENTS

WO WO 98/05289 2/1998

OTHER PUBLICATIONS

International Search Report of International Application No. PCT/US03/14435, filed May 9, 2003, mailed Jan. 19, 2005.

(Continued)

*Primary Examiner* — Tammie K Heller
(74) *Attorney, Agent, or Firm* — Morrison & Foerster LLP

(57) ABSTRACT

The methods and apparatus for lead placement on a surface of the heart are employed using an elongated body having proximal and distal end portions. The body defines a lead receiving passageway extending between a proximal inlet and a distal outlet for receiving a lead therethrough for contact with the heart surface. The elongated body is adapted for insertion between a pericardium and an epicardial surface. At least a portion of the body may have a non-circular cross-sectional shape adapted to retain the body orientation between the pericardium and the epicardial surface.

18 Claims, 23 Drawing Sheets

(56) References Cited

U.S. PATENT DOCUMENTS

| | | |
|---|---|---|
| 4,991,603 A | 2/1991 | Cohen et al. |
| 4,998,975 A | 3/1991 | Cohen et al. |
| 5,033,477 A | 7/1991 | Chin et al. |
| 5,106,580 A | 4/1992 | Mudiam |
| 5,213,570 A | 5/1993 | VanDeripe |
| 5,243,977 A | 9/1993 | Trabucco et al. |
| 5,269,326 A | 12/1993 | Verrier |
| 5,306,234 A | 4/1994 | Johnson |
| 5,336,231 A | 8/1994 | Adair |
| 5,336,252 A | 8/1994 | Cohen |
| 5,385,156 A | 1/1995 | Oliva |
| 5,423,821 A | 6/1995 | Pasque |
| 5,433,730 A | 7/1995 | Alt |
| 5,498,228 A | 3/1996 | Royalty et al. |
| 5,520,701 A | 5/1996 | Lerch |
| 5,582,580 A | 12/1996 | Buckman, Jr. et al. |
| 5,634,895 A | 6/1997 | Igo et al. |
| 5,676,162 A | 10/1997 | Larson, Jr. et al. |
| 5,676,651 A | 10/1997 | Larson, Jr. et al. |
| 5,678,547 A | 10/1997 | Faupel et al. |
| 5,681,278 A | 10/1997 | Igo et al. |
| 5,682,906 A | 11/1997 | Sterman et al. |
| 5,683,445 A | 11/1997 | Swoyer |
| 5,693,091 A | 12/1997 | Larson, Jr. et al. |
| 5,702,430 A | 12/1997 | Larson, Jr. et al. |
| 5,707,336 A | 1/1998 | Rubin |
| 5,716,392 A | 2/1998 | Bourgeois et al. |
| 5,725,521 A | 3/1998 | Mueller |
| 5,728,151 A | 3/1998 | Garrison et al. |
| 5,752,526 A | 5/1998 | Cosgrove |
| 5,766,189 A | 6/1998 | Matsuno |
| 5,797,870 A | 8/1998 | March et al. |
| 5,797,946 A | 8/1998 | Chin |
| 5,799,661 A | 9/1998 | Boyd et al. |
| 5,800,414 A | 9/1998 | Cazal |
| 5,823,946 A | 10/1998 | Chin |
| 5,823,955 A * | 10/1998 | Kuck et al. .................... 600/374 |
| 5,827,216 A | 10/1998 | Igo et al. |
| 5,840,059 A | 11/1998 | March et al. |
| 5,865,791 A | 2/1999 | Whayne et al. |
| 5,871,531 A | 2/1999 | Struble |
| 5,879,375 A | 3/1999 | Larson, Jr. et al. |
| 5,882,299 A | 3/1999 | Rastegar et al. |
| 5,895,298 A | 4/1999 | Faupel et al. |
| 5,897,586 A | 4/1999 | Molina |
| 5,900,433 A | 5/1999 | Igo et al. |
| 5,910,124 A | 6/1999 | Rubin |
| RE36,269 E | 8/1999 | Wright |
| 5,931,787 A | 8/1999 | Dietz et al. |
| 5,941,819 A | 8/1999 | Chin |
| 5,947,953 A | 9/1999 | Ash et al. |
| 5,961,440 A | 10/1999 | Schweich, Jr. et al. |
| 5,964,699 A | 10/1999 | Rullo et al. |
| 5,968,010 A | 10/1999 | Waxman et al. |
| 5,984,866 A | 11/1999 | Rullo et al. |
| 5,984,917 A | 11/1999 | Fleischman et al. |
| 5,991,668 A | 11/1999 | Leinders et al. |
| 5,997,525 A | 12/1999 | March et al. |
| 6,006,122 A | 12/1999 | Smits |
| 6,015,382 A | 1/2000 | Zwart et al. |
| 6,059,750 A | 5/2000 | Fogarty et al. |
| 6,081,738 A | 6/2000 | Hinohara et al. |
| 6,083,153 A | 7/2000 | Rullo et al. |
| 6,090,042 A | 7/2000 | Rullo et al. |
| 6,095,968 A | 8/2000 | Snyders |
| 6,110,170 A | 8/2000 | Taylor et al. |
| 6,120,431 A | 9/2000 | Magovern et al. |
| 6,148,230 A | 11/2000 | KenKnight |
| 6,149,595 A | 11/2000 | Seitz et al. |
| 6,155,968 A | 12/2000 | Wilk |
| 6,157,852 A | 12/2000 | Selmon et al. |
| 6,162,195 A | 12/2000 | Igo et al. |
| 6,167,889 B1 | 1/2001 | Benetti |
| 6,199,556 B1 | 3/2001 | Benetti et al. |
| 6,200,303 B1 | 3/2001 | Verrior et al. |
| 6,206,004 B1 | 3/2001 | Schmidt et al. |
| 6,221,007 B1 | 4/2001 | Green |
| 6,224,584 B1 | 5/2001 | March et al. |
| 6,237,605 B1 | 5/2001 | Vaska et al. |
| 6,241,667 B1 | 6/2001 | Vetter et al. |
| 6,258,021 B1 | 7/2001 | Wilk |
| 6,266,550 B1 | 7/2001 | Selmon et al. |
| 6,283,127 B1 | 9/2001 | Sterman et al. |
| 6,293,906 B1 | 9/2001 | Vanden Hoek et al. |
| 6,296,630 B1 | 10/2001 | Altman et al. |
| 6,311,692 B1 | 11/2001 | Vaska et al. |
| 6,311,693 B1 | 11/2001 | Sterman et al. |
| 6,312,404 B1 | 11/2001 | Agro et al. |
| 6,314,962 B1 | 11/2001 | Vaska et al. |
| 6,314,963 B1 | 11/2001 | Vaska et al. |
| 6,319,201 B1 | 11/2001 | Wilk |
| 6,333,347 B1 | 12/2001 | Hunter et al. |
| 6,352,503 B1 | 3/2002 | Matsui et al. |
| 6,423,051 B1 | 7/2002 | Kaplan et al. |
| 6,488,689 B1 | 12/2002 | Kaplan et al. |
| 6,917,834 B2 | 7/2005 | Koblish et al. |
| 7,004,173 B2 | 2/2006 | Sparks et al. |
| 7,226,458 B2 | 6/2007 | Kaplan et al. |
| 7,318,829 B2 | 1/2008 | Kaplan et al. |
| 7,610,104 B2 | 10/2009 | Kaplan et al. |
| 2002/0087208 A1 * | 7/2002 | Koblish et al. ................ 607/113 |
| 2002/0099390 A1 | 7/2002 | Kaplan et al. |
| 2002/0103492 A1 | 8/2002 | Kaplan et al. |
| 2002/0111637 A1 | 8/2002 | Kaplan et al. |
| 2003/0212446 A1 | 11/2003 | Kaplan et al. |
| 2007/0156217 A1 | 7/2007 | Kaplan et al. |
| 2007/0156220 A1 | 7/2007 | Kaplan et al. |

OTHER PUBLICATIONS

Final Office Action mailed on Nov. 29, 2006, for U.S. Appl. No. 10/144,205, filed May 10, 2002, 12 pages.
Final Office Action mailed on Nov. 13, 2007, for U.S. Appl. No. 10/144,205, filed May 10, 2002, 12 pages.
Final Office Action mailed on Nov. 13, 2008, for U.S. Appl. No. 10/144,205, filed May 10, 2002, 17 pages.
Final Office Action mailed on Apr. 14, 2010, for U.S. Appl. No. 11/687,334, filed Mar. 16, 2007, 10 pages.
Final Office Action mailed on May 7, 2010, for U.S. Appl. No. 11/687,320, filed Mar. 16, 2007, 8 pages.
Non-Final Office Action mailed Mar. 16, 2006, for U.S. Appl. No. 10/144,205, filed May 10, 2002, 10 pages.
Non-Final Office Action mailed on May 8, 2007, for U.S. Appl. No. 10/144,205, filed May 10, 2002, 12 pages.
Non-Final Office Action mailed on Apr. 11, 2008, for U.S. Appl. No. 10/144,205, filed May 10, 2002, 12 pages.
Non-Final Office Action mailed on Apr. 2, 2009, for U.S. Appl. No. 11/687,334, filed Mar. 16, 2007, 10 pages.
Non-Final Office Action mailed on Sep. 23, 2009, for U.S. Appl. No. 11/687,320, filed Mar. 16, 2007, 7 pages.
Notice of Allowance mailed on Jun. 15, 2009, for U.S. Appl. No. 10/144,205, filed May 10, 2002, 10 pages.

* cited by examiner

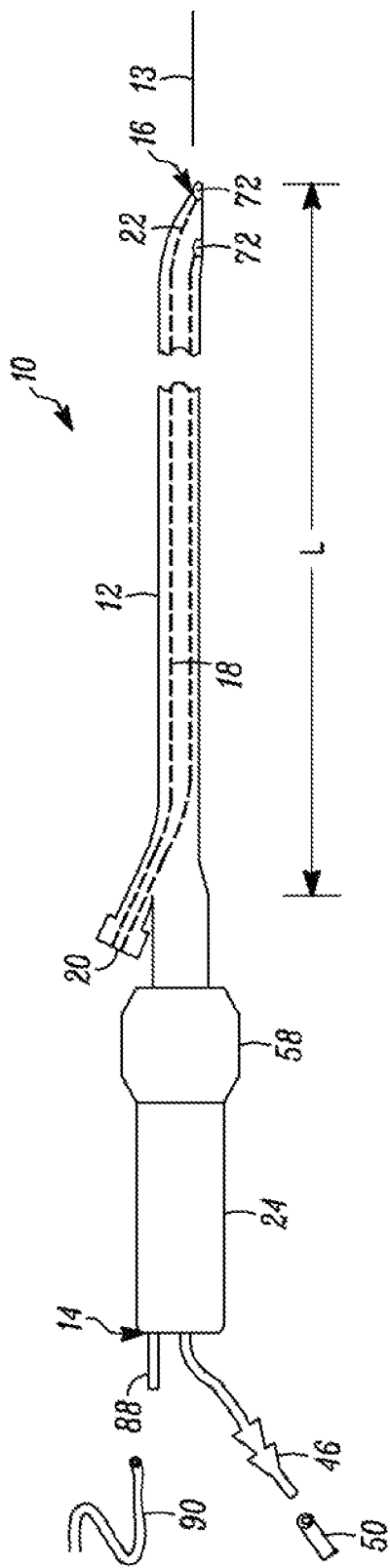
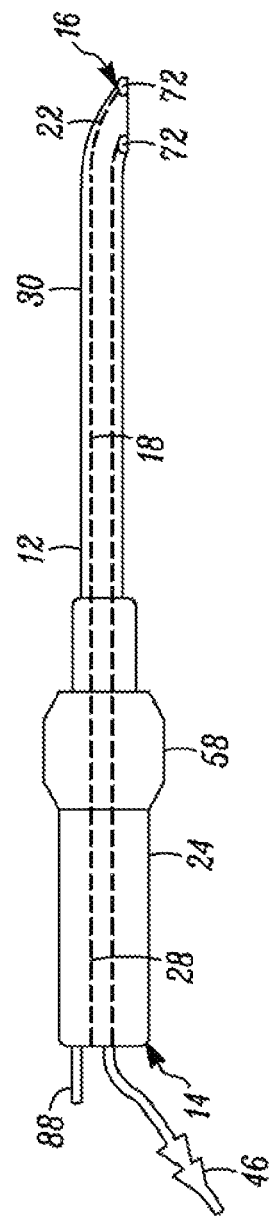
FIG. 1
FIG. 2

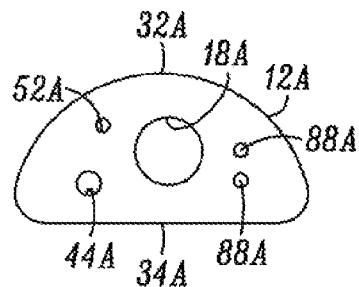
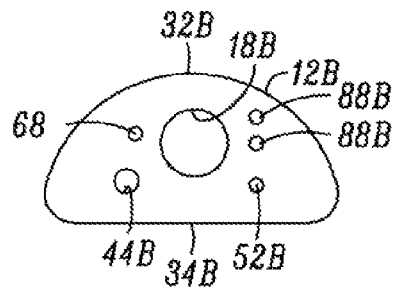
FIG. 5A          FIG. 5B
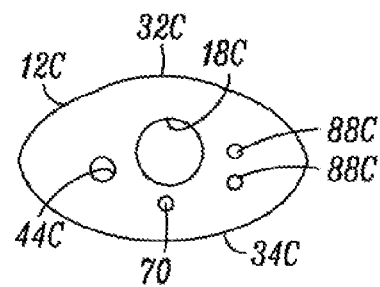
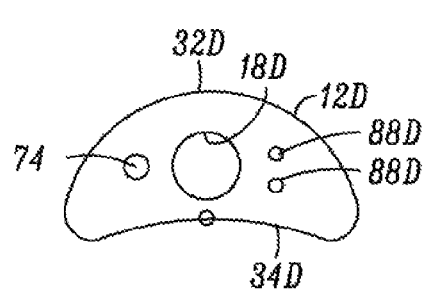
FIG. 5C          FIG. 5D
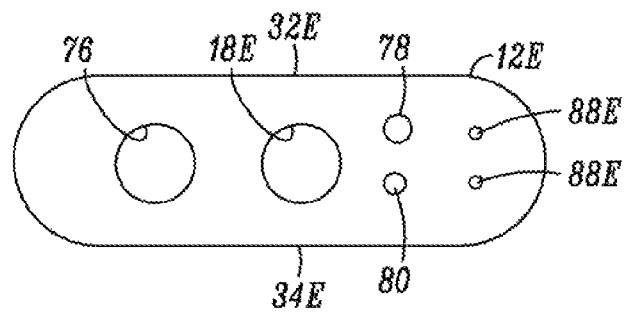
FIG. 5E

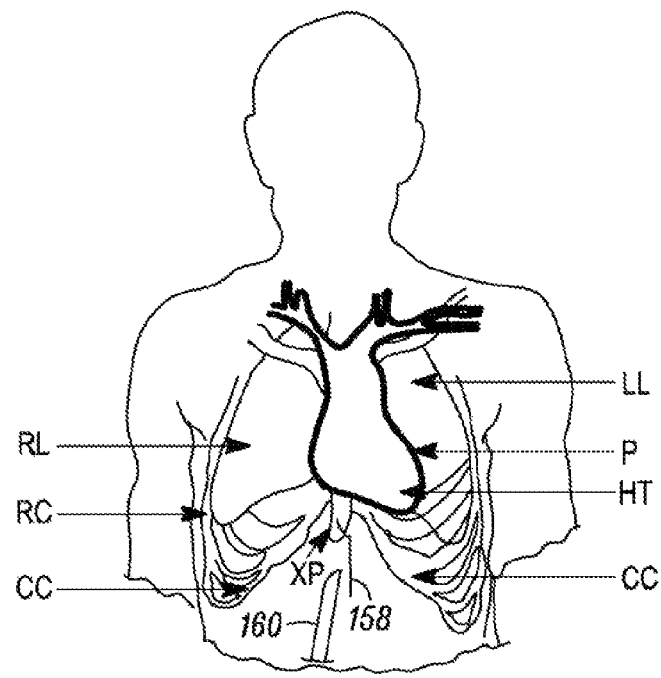
*FIG. 14*
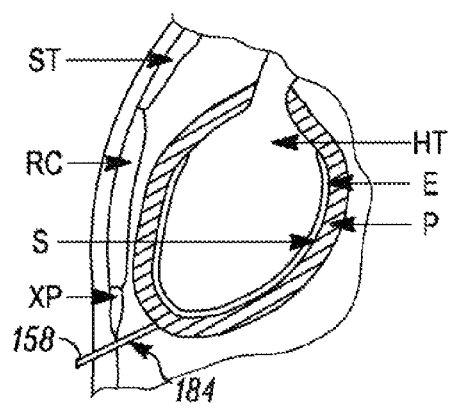 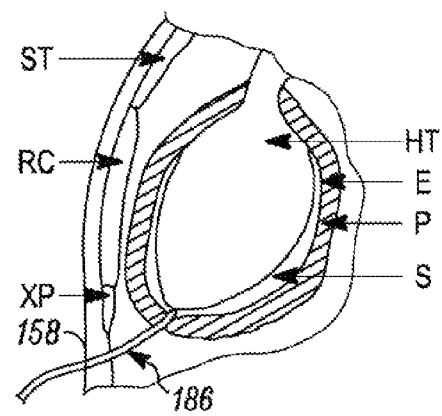
*FIG. 14A*　　　　　　*FIG. 14B*

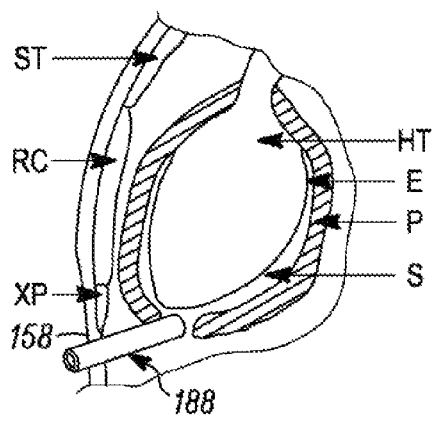
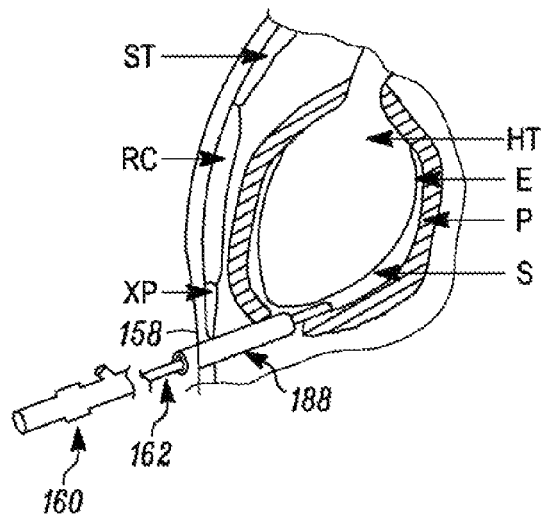
FIG. 14C        FIG. 14D
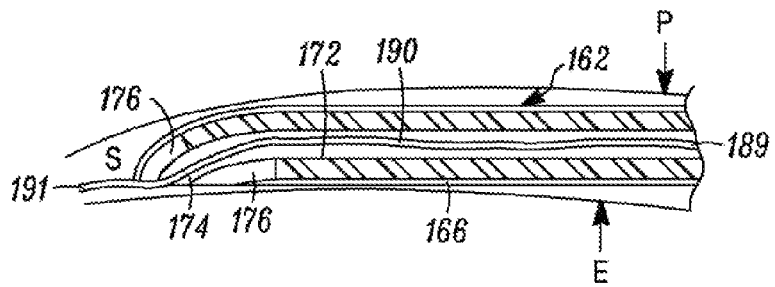
FIG. 15
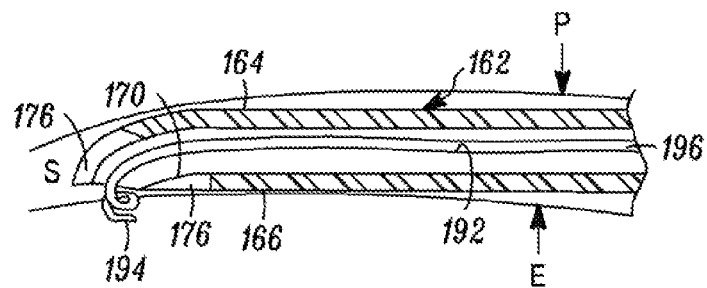
FIG. 16

METHODS AND APPARATUS FOR LEAD PLACEMENT ON A SURFACE OF THE HEART

RELATED APPLICATIONS

This is a divisional of U.S. patent application Ser. No. 10/144,205 titled, METHODS AND APPARATUS FOR LEAD PLACEMENT ON A SURFACE OF THE HEART, filed on May 10, 2002, now issued as U.S. Pat. No. 7,610,104, herein incorporated by reference in its entirety.

BACKGROUND

This invention relates to methods and apparatus for lead placement and other related procedures on or in connection with the heart.

Leads are conductive devices or electrodes for temporary or permanent contact or implantation on a heart surface. Leads are well known in the art and commonly have an elongated shape and include a distal end, typically with an electrode alone or in combination with a retention member, such as spiral or barbed, located thereon for attachment to the desired heart surface.

Leads carry electrical signals to and from the heart for a variety of purposes. One purpose, among many, of lead implantation is to allow pacing of the heart so as to restore the normal sequence of mechanical contractions to the heart. By way of example, but not limitation, leads may be placed on a surface of the heart in conjunction with a biventricular pacemaker, which generates a pacing signal. A proximal end of the lead is connected to the pacemaker while the distal end of the lead is attached to the desired heart location to carry the electrical signal to the heart. Temporary leads may also be used to monitor heart performance, to "map" the heart to identify conductive pathways, to identify sources of aberrant electrical pulses and to carry out various other diagnostic and/or therapeutic procedures.

A myriad of lead implantation sites relative to treatment of the human heart are also possible. Leads may be placed on an outer (epicardial) surface of the heart, implanted within the heart on an interior (endocardial) heart surface, or placed within the coronary sinus. The human heart is generally situated in a multi-layer membrane or heart sac, commonly known as the pericardium. The space between the pericardium and the outer or epicardial surface of the heart is commonly called the pericardial space. Although it may be technically possible to place leads on the outer surface of the pericardium, it is preferred to place leads within the pericardial space so as to improve the conductivity of the electrical path between the lead and the selected heart tissue.

Current apparatus and methods for epicardial lead placement often utilize non-minimally invasive medical procedures. These methods may involve a large incision into the chest, thoracotomy or medial sternotomy of a patient and/or opening of the chest cavity for access to the heart. These procedures typically may require the patient to be generally anesthetized, selectively intubated with collapse of a lung. A further major disadvantage of these procedures is that they may require a chest tube following surgery and are often associated with a painful postoperative course.

Sub-xyphoid access to the heart surfaces has been previously proposed by one of the inventors here in U.S. patent application Ser. No. 09/315,601 filed May 20, 1999 and is incorporated by reference herein. One potential difficulty which needs to be overcome when using the sub-xyphoid route for lead placement is the need for a substantial distal portion of the lead to be orthogonally disposed relative to the selected lead placement site in order to adequately attach the lead on the heart surface. In other words, it has been previously considered that the incident angle of approach of the lead placement apparatus should be disposed at a nearly perpendicular angle relative to the heart surface in order to position the distal outlet in a desired direction for lead placement. Because the angle of approach is so large, it requires a large working volume within the pericardial space. The working space required by the apparatus thus displaces a greater amount of cardiac tissue, which can increase the risk of complications during and after surgery. Therefore, there is a need for apparatus and methods for lead placement which avoid these shortcomings.

Several devices and methods for minimally invasive access to the epicardial surface of the human heart have been described in co-pending application Ser. No. 09/315,601 filed May 20, 1999, and Ser. No. 09/397,392 filed Sep. 16, 1999, both of these applications are hereby incorporated by reference in the present application.

Another drawback of current lead placement apparatus and methods is that they do not typically incorporate the ability to navigate over the surfaces of the heart for optimal lead placement. In one aspect, it would be desirable to provide an apparatus which permits temporary pacing of the heart so as to determine the optimal lead placement site prior to attachment of the lead to the heart surface. Pacing by temporary electrodes or leads prior to attachment of a permanent lead better ensures that the lead is properly attached to the desired heart location. In another aspect, it would be desirable to have a lead placement apparatus which prevents lead deposition in proximity to a coronary artery. Since coronary arteries surround the exterior of the heart, there is a danger that lead implantation could pierce the artery, resulting in possible bleeding into the pericardial space which may lead to hemodynamic compromise and collapse. Placement of an epicardial lead onto a coronary artery may occlude the artery resulting in infarction of the myocardium perfused by that artery. So, it would be desirable to provide a lead placement apparatus which has the ability to sense when the lead placement apparatus is unduly close to a coronary artery.

Current lead placement devices also do not provide relative positioning of the distal end of the device so as to orient the distal end in the desired direction for lead placement. Since the surface of the heart is not flat or uniform, the ability to position the distal end against the desired lead placement location is also desirable. Even once the lead placement site is located, the lead placement apparatus desirably should facilitate lead removal from the apparatus.

Accordingly, it is a general object of the present invention to provide a minimally invasive method and apparatus for placing a lead on a surface of the heart.

Another object of the present invention is to provide for an apparatus and method for lead placement, which apparatus has a geometry specifically suited for lead placement.

It is the object of another aspect of the present invention to provide a method and apparatus for temporary pacing of the heart prior to lead placement or in connection with mapping the conductive pathways of the heart tissue.

It is another object of the present invention to provide a method and apparatus for detecting proximity to the coronary arteries so as to avoid placement of the lead on or near a coronary artery.

It is a further object of the present invention to provide a method and apparatus which provides a distal end of the apparatus which is adapted to move in at least one plane when force is applied to the apparatus.

It is yet another object of the present invention to provide a method and apparatus having an expandable member to hold the apparatus adjacent the epicardial surface for lead placement.

A further object of the present invention is to provide a lead placement apparatus which facilitates lead removal.

A yet further object of the present invention is to provide a minimally invasive lead placement apparatus having a distal end portion which has an acute angle relative to the longitudinal axis for lead placement.

These objectives are provided to illustrate the context of the present invention and are not an exclusive listing of the objectives or benefits of the present invention. Not all of these objectives are necessarily met in each apparatus or method of the present invention. Apparatus or methods of the present invention may meet or address one or more, but less than all, of these objects or other objects or benefits of the invention apparent in other parts of this description. Therefore, these objectives are not presented for, and should not be used for, the purpose of limiting the scope of the invention as set forth in the appended claims.

SUMMARY

The features and objects of the present invention will become apparent upon reference to the following detailed description and attached drawings. Generally speaking, in accordance with one aspect of the present invention, the apparatus includes an elongated body or sheath having a proximal end portion, a distal end portion, and defines a passageway having a proximal inlet and a distal outlet for receiving a lead or conductive member. The distal outlet is generally located adjacent the distal end portion of the body.

The present invention is particularly well suited for providing a method and apparatus for placing a lead on a surface of the heart, where a substantial length of the body is adapted for insertion between a pericardium and an epicardial surface and the body is adapted for directional control by the user to position the distal outlet at a desired location between the pericardium and the epicardial surface.

At least a portion of the elongated body also may have a non-circular shape which is adapted to retain the body at a selected angular orientation between the pericardium and the epicardial surface. The non-circular shape may be comprised of convex, concave and planar surfaces, as will be described below. The body may further include a plurality of lumens or passageways for receiving, connecting to, or accommodating a variety of elements such as, for example, a vacuum, an inflation source, an irrigation source, a guide wire, an endoscope, a fiberoptic viewing device, temporary pacing electrodes, a Doppler sensor, a steering member, an expandable member, a flexible or malleable shape-retaining wire, or other like elements for facilitating lead placement in addition to other purposes which will be apparent to one skilled in the art. It is submitted that there are numerous combinations of all or some of these elements and that the combinations shown and described are by way of example and are not intended to limit the scope of the claimed invention.

Several mechanisms may be utilized in order to position the distal outlet of the body against the selected lead placement site. One way to move the distal end portion of the body is accomplished by employing at least one steering member extending through the elongated body having a distal and proximal end. The steering member moves when force is applied to the proximal end of the steering member. The force may be tensile, compressive or torsional, or a combination thereof. A steering collar can be positioned on the body spaced from the distal end portion to control one or more of the steering members. The steering collar is movable to supply tensile, compressive or torsional movement to the steering members. Movement of the steering members allows movement of the distal end portion of the body in at least one plane although movement in more than one plane is also possible.

In addition to the steering members, other ways to position the distal end portion of the body utilize a vacuum lumen, an expandable member, and/or a flexible or malleable element. The vacuum lumen may extend through the body between the proximal end portion, which is connected to a vacuum source, and the distal end portion which defines a distal opening of the vacuum lumen so as to create a suction force at the distal outlet and maintain the distal outlet biased against the selected lead placement site. Biasing of the distal outlet against the selected site can also be performed by selective expansion of the expandable member which is carried by the body and disposed in proximity to the distal outlet. One or more expandable members can be utilized and are adapted to expand after insertion of the body into the pericardial space and, by way of example but not limitation, the expandable member may include a balloon and inflation lumen, which fluidly communicates between the balloon and an inflation source, an expandable cage-like member or members, or the like. The expandable members may be mounted at the distal end in an eccentric or concentric fashion. The body may include at least one flexible or malleable wire which preferably, but not exclusively, extends through at least a portion of the body extending from the distal end portion and the flexible wire is well suited to retain a desired shape corresponding to the surface of the selected lead placement site so as to orient the distal end portion of the body for lead placement. Any of the aforementioned ways, either by themselves or in any combination thereof, as well as others may be employed to position the distal outlet against the selected lead placement site.

The present invention also provides a method and apparatus having a body including at least one temporary pacing electrode disposed in proximity to the distal end portion for contact with the surface of the heart. The temporary pacing electrode may be used in connection with placing a lead on a surface of a human heart and/or allow for the conductive pathways of the heart to be mapped for a variety of purposes. A conductor extends through the elongated body from the electrode to the proximal end portion of the body for attachment to an electric pacing signal source. The temporary pacing electrode is adapted to pace the heart by contact with selected one of a pericardial and epicardial surface. The temporary pacing electrode may be fixed at the distal end or removably inserted through the body.

In another aspect of the invention, the body of the lead placement apparatus defines a passageway which includes at least one outlet adapted to receive an elongated guide wire and a lead. The passageway has a lead outlet which is sufficiently sized to allow passage of the lead for attachment to the surface of the heart. The lead outlet tapers to a guide wire outlet which is distally located on the body in relation to the lead outlet. The guide wire outlet is sufficiently sized and oriented to allow passage of the guide wire forward of the distal end of the body and to deflect the lead to exit at an angle relative to the longitudinal axis of the body for engagement with heart tissue.

The present invention also discloses a lead placement apparatus and method for sensing the presence of a coronary artery so as to avoid placement of the lead into a coronary artery. The body includes a Doppler sensor disposed in proximity to the distal outlet and the Doppler sensor is in communication with an operator-readable output device to indicate the presence of a coronary artery in proximity to the distal outlet.

The present invention further provides an improved epicardial lead construction for ease of placement on an epicardial surface of the heart.

BRIEF DESCRIPTION OF THE DRAWINGS

FIG. 1 is a side view of a first embodiment of a lead placement apparatus of the present invention.

FIG. 2 is a side view of a second embodiment of a lead placement apparatus of the present invention.

FIGS. 4A-4C are sectional views of the distal end portion along the lines indicated in FIG. 4 and illustrating the non-circular cross-sectional shape of at least a portion of the body.

FIG. 5A is a sectional view of the distal end portion, similar to FIG. 4C, including a single steering member.

FIG. 5B is a sectional view of the distal end portion, similar to FIG. 4C, including a dedicated guide wire lumen.

FIG. 5C is a sectional view of the distal end portion, similar to FIG. 4C, including a flexible element and having an alternate non-circular cross-sectional shape.

FIG. 5D is a sectional view of the distal end portion, similar to FIG. 4C, including an inflation lumen and having another non-circular cross-sectional shape.

FIG. 5E is a sectional view of the distal end portion, similar to 4C, including an endoscope lumen and a fluid delivery lumen and illustrating yet another non-circular cross-sectional shape.

FIG. 14 is an anterior plan view of a patient's chest showing an incision via the sub-xyphoid region.

FIGS. 14A-14D are sectional elevation views of a patient's chest showing access to the pericardial space via a sub-xyphoid approach.

FIG. 15 is a longitudinal cross-section of the distal end portion of the lead placement apparatus taken along line 15-15 of FIG. 17, showing insertion of a guide wire into the pericardial space.

FIG. 16 is a longitudinal section taken along line 1616 of FIG. 17 which shows insertion of a lead into the pericardial space.

DETAILED DESCRIPTION

Figure 3:
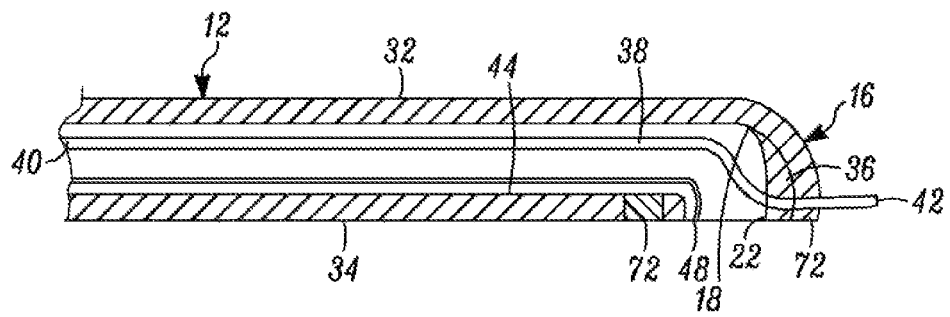
FIG. 3 is a sectional view of a distal end portion of the lead placement apparatus.

The present invention provides methods and apparatus for placing a lead on a surface of a human heart. Although the invention will be described by way of example but not limitation in relation to epicardial lead placement, placement of the lead on other heart surfaces is also possible. Such heart surfaces may also include the pericardium and the endocardial surface in addition to the epicardial surface. The manner in which the lead is placed on the heart surface may also vary. By way of example but not limitation, the lead may be implanted or embedded into the surface using a retention member or fastener which penetrates beneath the surface. Different types of retention members may be utilized and it is not intended for the present invention to be limited only to those retention members shown in the drawings since it is realized that many variations may be used to effectuate lead retention without departing from the present invention. Moreover, the lead may be placed on the heart surface for either temporary or permanent use, as needed.

As shown in FIG. 1, a first embodiment of a lead placement apparatus 10 of the present invention includes an elongated body 12 and defines a longitudinal axis 13. The body 12 includes a proximal end portion generally at 14 and a distal end portion generally at 16. The body 12 defines a lead receiving passageway 18 which extends between a proximal inlet 20 and distal outlet 22. The lead receiving passageway 18 is adapted and suitable to receive a lead for attachment to the surface of the heart. The lead is shown, by way of example, in FIG. 16 which will be described below. At the proximal end portion 14 of the body 12, a handle 24 may be provided. A preferred approach utilizes a sub-xyphoid approach to place the lead on a heart surface. Other approaches may be utilized without departing from the scope of the claimed invention, such as, for example, intercostal, intravenous and other minimally invasive approaches as well as more invasive approaches, such as open chest procedures.

The elongated body 12 preferably has sufficient length so as to allow insertion of at least the distal end portion 16 of the body from a sub-xyphoid transcutaneous access opening to the area between the pericardium and the epicardial surface and into a space which is commonly referred to either as the pericardial space. The length of the body will depend on which medical approach is used to gain access to the heart surface. Importantly, the length of the body should be such that the handle 24 remains outside of the patient while the medical procedure is performed so as to allow greater control over the lead placement apparatus. By way of example but not limitation, the length L of the body 14 between the proximal inlet and the distal outlet 22 has a length and a range of 10 cm to 40 cm, preferably 20 cm to 30 cm where a sub-xyphoid approach is used, so that the proximal inlet 20 is located outside of the patient.

In FIG. 1 the proximal inlet 20 is disposed at generally the proximal end portion 14 of the body 12, although it is spaced from the proximal tip end of the handle. The length L of the body 12 allows extension of the distal end portion 16 into the pericardial space while, at the same time, allowing the proximal inlet 20 to extend outside into the pericardial space and, preferably, outside of the incision access location into patient's body. In this way, the proximal inlet 20 is accessible to allow insertion of the lead therein. It is also possible to position the proximal inlet at other longitudinal positions along the body 12 as is indicated in FIG. 2 in an alternate apparatus 26, with like parts being shown with like numbers, except that the proximal inlet 28 is positioned at the most proximal end of the handle 24. The apparatus 26 similarly has a length which is sized to allow insertion of the distal end portion 16 into the pericardial space and access to the handle 24 and proximal inlet 20 from the outside of the incision access location.

Non-Circular Shape

Figure 4:
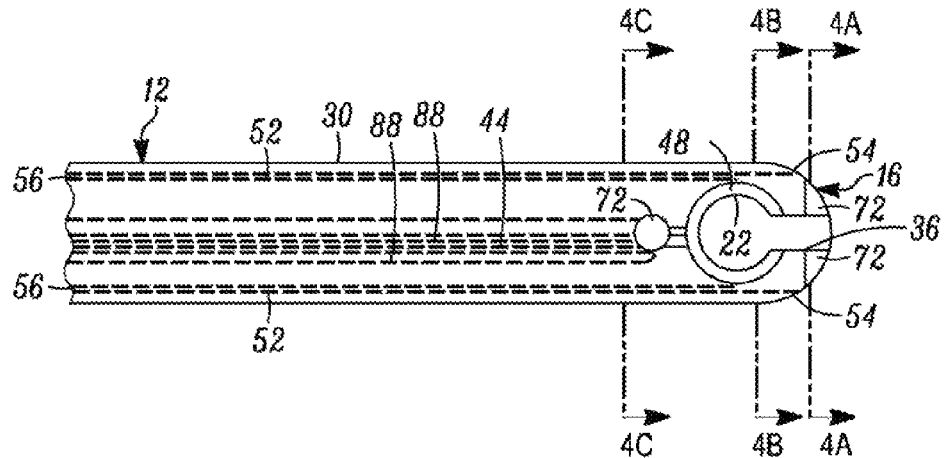
FIG. 4 is a bottom view of the distal end portion of the lead placement apparatus.
Figure 4C:
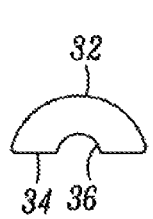
Figure 4C:
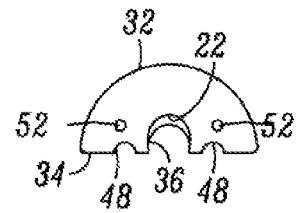
Figure 4C:
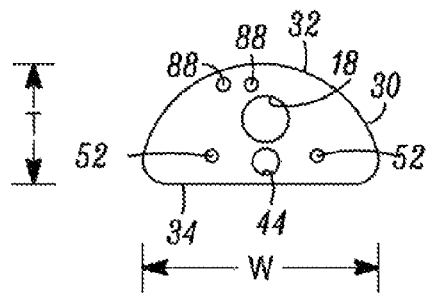

Turning to FIGS. 4-4C, at least a portion of the elongated body 12 may have in certain, but not all embodiments of the present invention, a non-circular shape, so described because it has a cross-section which is non-circular as best seen in FIGS. 4 and 5. The non-circular shape may appear in a myriad of different forms, some of which will be shown and described below, but other non-circular shapes are also possible without departing from the present invention. The non-circular shape is associated with at least a portion of the body, preferably, the portion of the body which is inserted into the pericardial space. For example, the non-circular shape extends along the body 12 between the proximal inlet 20 and the distal outlet 22 in FIG. 1 or between a portion thereof. In the most preferred form, the portion of the body 12 which contacts the heart surface such as the distal end portion 16 has a non-circular shape. As shown in FIGS. 3-4C, the non-circular shape of the body 12 is generally constant along the body except near the distal end portion 16 where the body gradually tapers.

In FIG. 4C the non-circular shape includes an upper surface 32 which is convex and a lower surface 34 which is planar. So the cross-sectional shape of the non-circular portion 30 in FIG. 4C has a "D" configuration. It is contemplated that the lower surface 34 faces the heart surface in which lead placement is desired and the upper surface 32 generally faces away from the desired lead placement site, although other orientations are also possible. As shown in FIGS. 3 and 4B the distal outlet 22 may be defined in the lower surface 34 near the distal end portion 16 of the body. So when the distal outlet 22 is placed adjacent the desire lead placement site, the lead can be advanced from the outlet opening in the lower surface 34 and directed at the heart tissue. It is realized that other locations of the distal outlet are possible without departing from the present invention.

As is illustrated best in FIG. 4C, the portion of the body with the non-circular shape preferably has a width, generally indicated at W, which is greater than its thickness, generally indicated at T. When the body is inserted into the pericardial space, the width of the body 12 is oriented in a generally parallel relationship to the heart surfaces. Relative to FIG. 4C, the lower surface 34 is disposed adjacent the epicardial surface and at least a portion of the upper surface 32 is disposed adjacent the pericardium. Likewise, the thickness of the body 12 is oriented in a generally perpendicular relationship with the heart surfaces, so the non-circular shape of the body attributes a slim profile when inserted into the pericardial space. Also, the working space existing within the pericardial space is more efficiently utilized, and displacement between the epicardial surface and pericardium is minimized when the body is inserted into the pericardial space. It can further be said that the non-circular shape of the body tends to retain the body at a selected angular orientation between the pericardium and the epicardial surface and prevents unplanned rotation of the body about its own axis. This assists in orienting the distal outlet in the desired direction so that it is pointed toward the heart surface.

FIGS. 5A-5E illustrate variations in the body 12 and like parts will be indicated with like numbers followed by a letter designation of A-E, as appropriate, which corresponds to the appropriate figure. FIGS. 5A and 5B show bodies, 12A and 12B, respectively, which are shaped similarly to the non-circular shaped body 12 in FIG. 4C, except that the internal arrangement of lumen is varied, as will be described later. FIG. 5C illustrates an alternate non-circular shape of a body 12C having an upper surface 32C and a lower surface 34C which are both convex so as to generally define an oval or eccentric shape. FIG. 5D illustrates another alternate non-circular shape of the body 12D having an upper surface 32D which is convex and a lower surface 34D which is concave. FIG. 5E illustrates a body 12E having an elongated oval shape where the upper and lower surfaces define substantially planar top and bottom portions which are joined by curved edge portions. The major axis of the oval is oriented along the width and the minor axis is oriented along the thickness.

As can be seen during insertion of the body 12 into the pericardial space using these alternate shapes, the upper surface 32 will be in contact with the pericardium and the lower surface 34 which includes the distal outlet of the lead receiving passageway will generally be in contact with the epicardial surface. As the non-circular portion generally has a width which is greater than its thickness and provides a relatively slim profile, insertion of the body into the pericardial space is facilitated. Also, the distal outlet 22 of the lead receiving passageway 18 is preferably located in the lower surface 34, which faces the epicardial surface. The non-circular shapes shown in the figures are by way of example but not limitation since other combinations may be utilized.

Turning back to FIGS. 3-4C, the distal end portion 16 of the body 12 illustrated there gradually narrows from a more proximal portion of the body. In particular, the body 12 narrows from the view shown in FIG. 4C to the successive view 4B and then 4A as the body extends to the distal end portion 16. Although the body is successively thinner in FIGS. 4A and 4B, than in FIG. 4C, the body 12 may retain a non-circular shape. FIGS. 4A and 4B also generally retain the relative proportions of the body where the width which is greater than the thickness.

Guide Wire Outlet

FIGS. 3-4B also illustrate a guide wire outlet 36 which is formed in the lower surface 34 of the body at the distal end portion 16. The guide wire outlet 36 is formed distally relative to the lead outlet or distal outlet 22 and, as shown in FIGS. 3 and 4, the guide wire outlet 36 is in communication with the distal outlet 22, and connects to the lead receiving passageway 18.

As shown in FIG. 3, a guide wire 38 is received by the lead receiving passageway 18 and is inserted from a more proximal portion of the body 12, such as from either of the proximal inlets 20 and 28 in FIGS. 1 and 2, respectively. The guide wire 38 has a proximal end 40 and a distal end 42 which extends forwardly, or distally, through the guide wire outlet 36.

In FIGS. 3-4B, the guide wire outlet 36 is generally defined as a channel extending longitudinally from the distal outlet 22 in the forward direction, similar to the entrance to an igloo. The guide wire outlet 36 is sufficiently sized and oriented to allow passage of the guide wire but prevent passage of the lead. As shown in FIGS. 3-4C, the guide wire outlet 36 is sized smaller than the lead outlet and longitudinally oriented in order to avoid extension of the lead beyond the distal end portion 16 of the body.

During use the distal end 42 of the guide wire extends forwardly of the distal end portion 16 so as to guide the apparatus 10 to the selected lead placement site. The guide wire also may bisect the tissue so as to provide a clear working space for lead placement. The guide wire may be removed from the body and successively thicker guide wires may be inserted. The lead receiving passageway 18 may be sized so that it is adapted to receive the guide wire and the lead during use or, alternatively, the guide wire may be removed from passageway 18 prior to lead insertion. After proper placement of the distal end is confirmed, the lead may be inserted. When the distal tip of the lead engages the end of the body, the curved inner surface deflects the lead downwardly through the distal outlet 22.

Steering Members

FIGS. 4 and 4C also illustrate steering members 52 disposed within the body 12. The steering wires 52 have a distal end 54 and a proximal end 56. The distal end 54 of the steering members is located at a position at or near the distal end portion 16 of the body and extends in a proximal direction towards the proximal end portion 14 of the body. The proximal end 56 of the steering members may extend from the proximal end portion 14 of the body 12 in a similar manner as described relative to the vacuum lumen 44 or it may extend to any of several intermediate positions of the body. The steering wires 52 may be operatively connected to a steering collar 58, as shown in FIGS. 1 and 2, which is disposed at a more proximal portion of the body 12 adjacent the handle 24 and accessible to the doctor.

The steering members 52 are made of a suitable material having an elongated shape such as wire, fiber, filament, surgical tape or the like although other materials and forms are possible without departing from the present invention. The steering member may include one or more separate members as shown in FIGS. 4 and 4C, which illustrates two steering members. By pulling on one member and pushing (or at least not pulling) the other, the distal end portion can be deflected in the desired direction. By reversing this action, the tip may be deflected in the opposite direction.

The body 12, and in particular, the handle 24 or steering collar 58 may include, various control elements such as levers, buttons, switches or the like to vary the application of force, the degree of curvature, and the direction of movement. The applied force may be tensile, compressive or rotational or any combination thereof. Tension and compression may be applied directly or indirectly to the steering member by pulling or pushing the steering member at any position along its length whereas rotation occurs by directly or indirectly twisting the steering member. The steering members may be used in combination with the vacuum lumen discussed above or, alternatively, in lieu of the vacuum lumen so as to orient the distal outlet in the desired direction for lead placement.

In the embodiment shown in FIGS. 4 and 4C, the steering members are each positioned on one side of the body and extend longitudinally relative to the body. So that within a first plane, tensile force applied to the proximal end 56 of the left steering member 52 in FIG. 4C will move the distal end portion 16 to the left. Similarly, tensile force applied to the proximal end of the right steering member in FIG. 4C will move the distal end portion to the right.

As mentioned previously, other types of forces or a combination thereof may be applied to the steering member either directly or indirectly. Also, force can be applied to the steering member so as to move the distal end portion 16 of the body in more than one plane. The resultant movement of the distal end portion 16 will depend on the number and location of steering members disposed within the body as well as the magnitude and type of forces applied. It is realized that one or more steering members may be positioned at different locations and orientations within the body so as to effectuate the desired movement of the distal end portion. Other combinations are possible without departing from the present invention.

By way of example but not limitation, FIGS. 5A and 5B illustrate alternate bodies 12A and 12B, respectively, each having a single steering member 52A and 52B, respectively. In FIG. 5A the steering member 52A is disposed in an upper left position. In FIG. 5B the steering member 52B is disposed in a lower right position. So, force applied either directly or indirectly to either steering member will cause deflection of the distal end portion 16.

Figure 21:
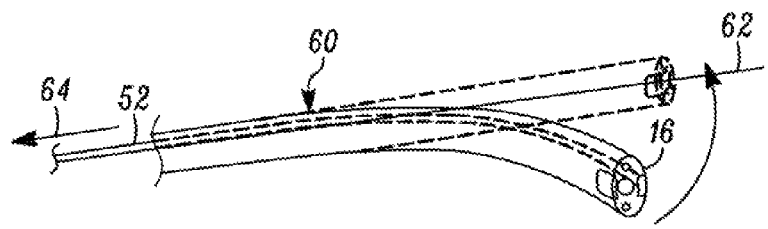
FIG. 21 is a perspective view of the lead placement apparatus showing movement between a normally curved position and a straight position by applying force to a steering wire.
Figure 22:
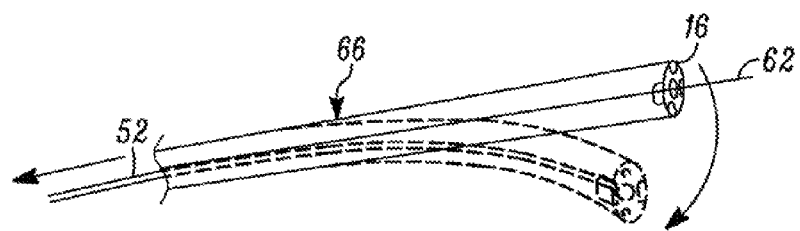
FIG. 22 is a perspective view of the lead placement apparatus showing movement between a normally straight position and a curved position by applying force to a steering wire.

In addition, movement of the steering member may increase or decrease the curvature of the distal end portion relative to the remainder of the body as illustrated in FIGS. 21 and 22. Turning briefly to FIGS. 21-22, these figures illustrate other aspects of the steering members of the present invention. In FIG. 21, a body 60 includes a steering member 52 which extends through the body to the distal end portion 16. The body 60 generally defines a longitudinal axis 62 and at least the distal end portion 16 of the body is curved relative to the axis when normally positioned and not acted upon by any force. The body may be curved, for example, to an angle between 10 degrees and 80 degrees relative to the longitudinal axis 62 and preferably between approximately 30 and 60 degrees. The normal or at rest position of the body is illustrated in solid lines and dashed lines represent a position of the body after force has been applied either directly or indirectly to the steering member. The force, indicated at 64, may be tensile, compressive or rotational or a combination thereof. When force is applied to the steering member 52, the distal end portion 16 moves to a less curved position as indicated by dashed lines.

An alternate body 66 is illustrated in FIG. 22, which likewise has a steering member 52 extending to the distal end portion 16. In this embodiment the distal end portion 16 is normally positioned in alignment with the longitudinal access 62 and force applied to the steering member 52 moves the distal end portion 16 of the body from the normally aligned straight position to a curved position relative to the longitudinal axis. It is realized that any type of force may be used to move the distal end portion of the body in one or more planes so that the distal end portion of the body may be curved relative to the longitudinal axis in one or more planes in the range approximately of 10 degrees to 80 degrees.

Figure 19:
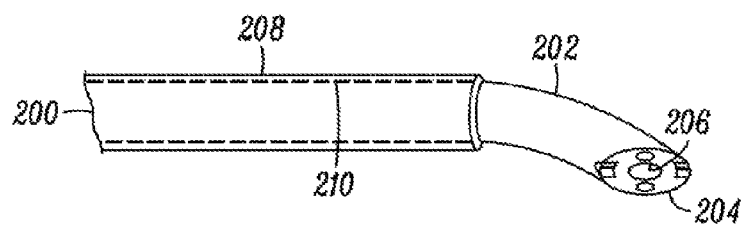
FIG. 19 is a perspective view of a sixth embodiment of the lead placement apparatus showing a portion of the apparatus being normally curved relative to the longitudinal axis.
Figure 20:
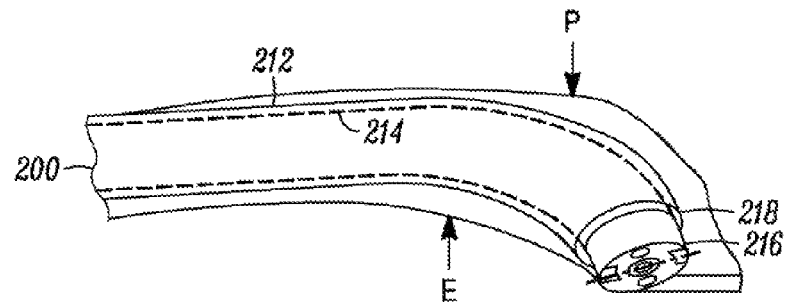
FIG. 20 is a perspective view of a seventh embodiment of the lead placement apparatus showing a normally straight portion of the apparatus being curved relative to the longitudinal axis as the result of a curved insertion sleeve.

Turning also to FIGS. 19 and 20, other steering features may be utilized in the present invention. FIGS. 19 and 20 show a least a portion of a body which is curved relative to a longitudinal axis 200. In FIG. 19 a body 202 having a distal end portion 204 is normally curved relative to the longitudinal axis 200 at the distal end portion. The body is made of a flexible or deformable material such as a polymer or plastic or may be made of a rigid material which is adapted to articulate. A distal outlet 206 is defined in the distal end portion for extension of the lead therethrough. The body 202 is slidably received in an elongated sleeve 208. The sleeve 208 has a rigid or semi-rigid, cylindrical shape and defines an inner lumen 210 which is sized sufficiently large to receive the body 202 for slidable movement. The sleeve diameter is slightly larger than the diameter of the body and preferably sized so as to fit snugly over the body and prevent incidental moving of the sleeve during insertion of the body into the pericardial space, although it is preferred that there be clearance between the proximal end of the sleeve and the proximal end of the body so as to permit axial movement of the sleeve on the body. The sleeve preferably has sufficient length so that during insertion of the sleeve and body into the pericardial space the sleeve extends from the distal end 206 of the body to a more proximal portion of the body which is located outside of the pericardial space for accessibility by the operator.

In FIG. 19, the sleeve 208 has a linear configuration so that when the sleeve is moved in a position where the sleeve 208 is positioned around the distal end 204 of the body, the body is temporarily deformed from its normally curved position to a straight configuration, which may be desired during introduction of the body initially into the patient's chest. When the body is inserted into the pericardial space, the sleeve 208 may be moved or retracted proximally relative to the distal end 204 so as to allow the portion of the body 202 which extends distally on the sleeve to resume its normally curved configuration, which may be at any angle between 10 degrees and 80 degrees relative to the longitudinal axis. Selective retraction of the sleeve may permit greater or lesser curvature of the body—depending on the length of the body that extends beyond the distal end of the sleeve.

FIG. 20 illustrates an alternative sleeve 212 having a curved portion relative to the longitudinal axis 200. An inner bore 214 sized to receive a body 216. A distal end 218 of the sleeve is curved relative to the longitudinal axis 200. The sleeve in FIG. 20 maintains the body 216 in a curved orientation relative to the longitudinal axis where the body, instead of being normally curved, may be normally straight. Then as the body 216 extends from the distal end 218 of the sleeve the distal end of the body will maintain an orientation in the direction pointed by the distal end of the sleeve, or in other words, which is in coaxial alignment with the distal end 218 of the sleeve. The angle of curvature of the sleeve may be between 10 degrees and 80 degrees, for example.

Plurality of Lumen

FIGS. 1-5E illustrate a plurality of lumens or passageways defined by the body 12 and these lumens or passageways are adapted to receive or accommodate a myriad of elements. These lumens or passageways may have a variety of different orientations although they generally extend between a distal end or opening and a proximal end or opening. FIGS. 5A-5E illustrate, in cross sectional views, various positions and combinations and orientations of the passageways within the lead placement apparatus, and are intended to be exemplary and not exclusive.

Turning to more particular embodiments, in FIGS. 1-4 and 4C, the body 12 defines a vacuum lumen 44, which extends between a proximal opening 46 and a distal opening 48. The proximal opening 46 is located at the proximal end portion 14 of the body. FIG. 1 illustrates the proximal opening 46 in the form of a rearwardly extending tube for attachment to a suction port of a vacuum source 50. In FIGS. 3 and 4, the distal opening 48 of the vacuum lumen 44 is formed as an annulus or C-shaped configuration partially around the distal outlet 22. This annulus provides a suction force at the distal outlet so as to help hold the distal outlet against the heart surface. Of course, other locations of the vacuum lumen distal opening are possible corresponding to alternate positions on the distal outlet 22. Alternate positions of the vacuum lumen 44 in the body are shown in FIGS. 5A-5C, as indicated by corresponding numbers 44A-44C.

FIGS. 5B-5E briefly illustrate other devices which may be introduced through the body and the associated lumen. For example, the body may include passageways, such as a guide wire lumen 68 (FIG. 5B), a lumen for an elongated flexible or malleable element 70 (FIG. 5C), an inflation lumen 74 (FIG. 5D), an endoscope lumen 76 (FIG. 5E), a fluid delivery lumen 78 (FIG. 5E), and a lumen for a Doppler sensor 80 (FIG. 5E). Each of these will be described in turn with reference to the appropriate figures.

Figure 17:
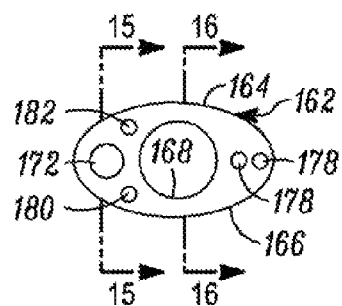
FIG. 17 is a transverse sectional view of the lead placement apparatus of FIGS. 15 and 16.

FIG. 5B illustrates a dedicated guide wire lumen 68 which extends between a guide wire inlet and a guide wire outlet. It is contemplated that the guide wire inlet can be located on a proximal portion of the body 12B. By way of example, but not limitation, the guide wire inlet may be positioned on the body as previously described relative to the proximal inlet 20 in FIGS. 1 and 2. Also, in a manner similar to the previously described guide wire outlet 36 in FIGS. 3 and 4, the guide wire outlet of the dedicated guide wire lumen 68 is preferably disposed generally in proximity to the distal outlet 22 although the exact location may vary. For example, the dedicated guide wire outlet may be positioned in the lower surface 34 adjacent the distal outlet or positioned, similar to the guide wire outlet 36 in FIGS. 3 and 4 (except that the guide wire would be dedicated or separate from the lead receiving passageway 18). Other locations for the dedicated guide wire outlet are, of course, possible without departing from the present invention. Additional views of the dedicated guide wire lumen of the present invention are provided by FIGS. 15-17 in accordance with an alternate body design. Turning briefly to FIGS. 15-17, a dedicated guide wire lumen 172 is defined within the body 162 and receives a guide wire 190 so as to facilitate identification of a selected lead placement site. Use of the guide wire will be more particularly described relative to FIGS. 15-17 below.

Figure 24:
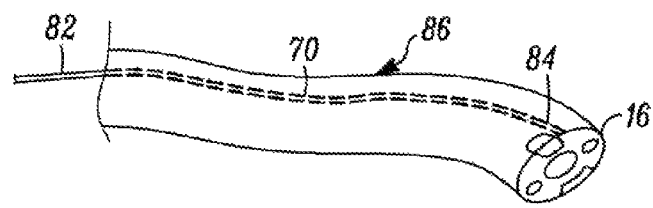
FIG. 24 is a perspective view of a ninth embodiment of the lead placement apparatus having a flexible or malleable element.

FIG. 5C illustrates the flexible or malleable element 70 in cross section which will be described in conjunction with FIG. 24. Turning to FIG. 24, the flexible element 70 includes a proximal end 82 and distal end 84, which is generally coextensive with the distal end portion 16 of the body 86. The element 70 is disposed within the body and suitable for manual forming into a desired shape, such as a shape which corresponds to a surface of the heart so as facilitate placement of the body 22 adjacent a heart surface. Both the element and the body are sufficiently flexible so as to allow the surgeon to change the curvature of the body.

The flexible element 70 may be in the form of one or more malleable wires or other like shape-retaining material. In FIG. 24, the flexible element has been formed with several curvatures along it length and the distal end portion 16 is curved relative to the longitudinal axis 13 of the body. The flexible element has the added characteristic that it is malleable, and retains the desired shape once it is positioned. Retention of the desired shape is generally maintained until repositioned by the user. It is also possible that the shape could be retained by various locking mechanisms utilized on or within the body.

FIG. 5D shows the body 5D of a lead placement apparatus which includes the inflation lumen 74. In a similar manner as the vacuum lumen 44, the inflation lumen generally extends between distal and proximal openings. This feature will be described further in relation to FIGS. 7-8.

In FIG. 5E, each of the endoscope lumen 76 and the fluid delivery lumen 78 similarly extend between distal and proximal openings. The endoscope lumen will be described further in FIGS. 8-10. Relative to the fluid delivery lumen 78, it permits an introduction of fluid to the heart surface at the selected lead placement site. The fluid delivery lumen may be connected in fluid communication with a fluid source at a proximal end of the lead placement apparatus. A distal opening of the fluid delivery lumen 78 is preferably disposed adjacent the distal outlet.

Temporary Pacing Electrodes

Turning back to FIGS. 1-4, the body 12 may further include at least one temporary pacing electrode 72. Although the temporary pacing electrode is shown in relation to a non-circular body, it is not intended to limit the temporary pacing electrode as such, and the temporary pacing electrode may be used in any of the illustrated body configurations or others not shown.

In FIGS. 1-4 one temporary pacing electrode 72 is positioned proximally relative to the distal outlet 22 and another temporary pacing electrode 72 is positioned distally relative to the distal outlet at the distal end portion 16 of the body 12. In FIG. 4 the distal temporary pacing electrode flanks the guide wire outlet 36. The temporary pacing electrodes are preferably disposed in proximity to the distal outlet 22 for contact with the surface of the heart when the body 12 is placed, for example, within the pericardial space, although other locations may also be suitable.

As shown in FIGS. 3 and 4C, a conductor 88 extends from each temporary pacing electrode 72 to a more proximal portion of the body 12. By way of example, the conductors 88 may extend to the proximal end portion 14 of the body for connection to an electrical pacing signal source, generally indicated at 90 in FIG. 1. Although the conductors are shown as positioned within the body, it is also possible that the conductors may extend outside at least a portion of the body.

Contact between a heart surface and the temporary pacing electrode allows temporary pacing of the heart prior to lead implantation. Temporary pacing allows different surface areas of the heart to be electrically stimulated, and the effect of such electrical stimulation can be monitored using appropriate devices which are apparent to one skilled in the art. After different areas of the heart are tested for their effect from temporary pacing, the optimal lead implantation site can be determined. The temporary pacing electrode may theoretically be adapted to pace the heart by contact with either one of the epicardial surface or the pericardium, although it is preferred that the temporary pacing electrode pace the heart by contact with the epicardial surface and the use of the temporary pacing electrodes will be described relative to contact with the epicardial surface.

FIGS. 5A-5E illustrate the conductors, corresponding to reference numerals 88A-88E, respectively, extending through the body, as previously described. The conductors generally extend parallel to the longitudinal axis of the body and, eventually, are connected to the pacing signal source. Variations are possible as to the location of the temporary pacing electrode along the body and within any of the various body shapes without departing from this aspect of the present invention. These alternate positions include but are not limited to the upper surface of the body.

Figure 6A:
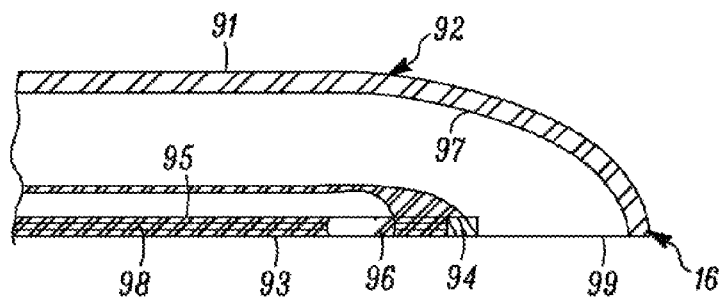
FIG. 6A is a sectional view, similar to FIG. 3, showing a third embodiment of a lead placement apparatus having a monopolar temporary pacing electrode.
Figure 6B:
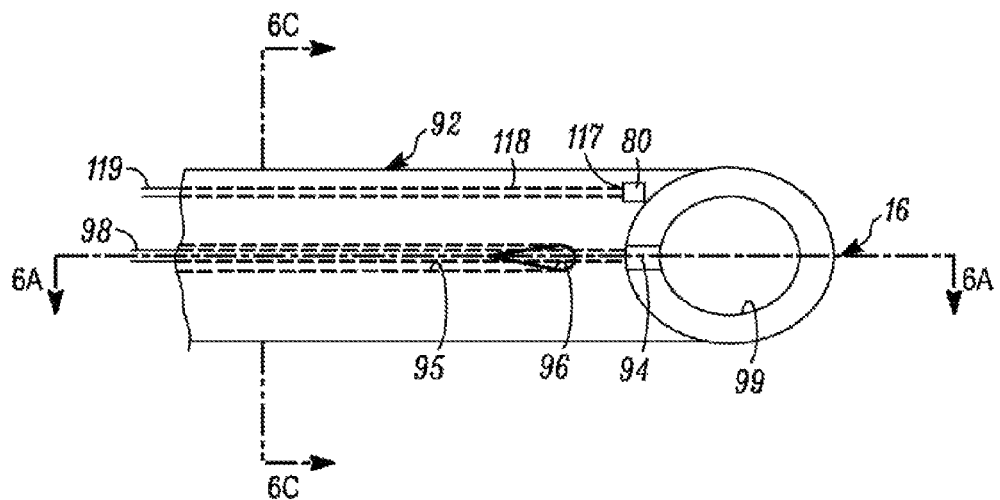
FIG. 6B is a bottom view of the embodiment shown in FIG. 6A.
Figure 6C:
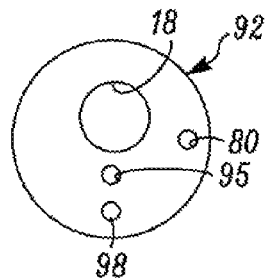
FIG. 6C is a sectional view along line 6C-6C in FIG. 6B.

FIGS. 6A-6C illustrate an alternate embodiment which includes a body, generally indicated at 92, having an upper surface 91 and a lower surface 93. A monopolar temporary pacing electrode 94 is located at the lower surface 93 of the body 92 (and could be located in the upper surface if desired). The body 92 also includes a vacuum lumen 95, a lead receiving passageway 97 with a distal outlet 99 and a Doppler sensor 80. The vacuum lumen 95 has a distal opening 96, which is rearwardly positioned relative to the distal outlet 22. The monopolar temporary pacing electrode 94 has a conductor 98 which extends along the body to a proximal portion of the body 92. In FIGS. 6A-6C the monopolar temporary pacing electrode 94 is located adjacent the distal outlet 22 so as to allow for pacing of the heart at a location closely adjacent to the outlet 99 to reflect the electrophysiological consequences of lead placement at that location prior to actual attachment of the lead. As discussed above in relation to FIG. 1, the monopolar temporary pacing electrode is connected via the conductor 98 to a suitable pacing signal source typically outside the patient's body.

Figure 23:
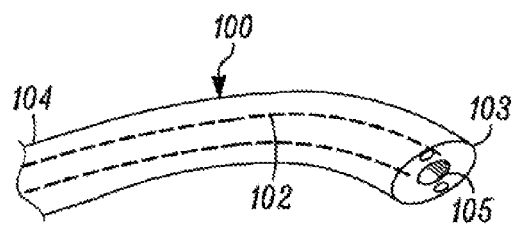
FIG. 23 is a perspective view of an eighth embodiment of the lead placement apparatus.
Figure 23A:
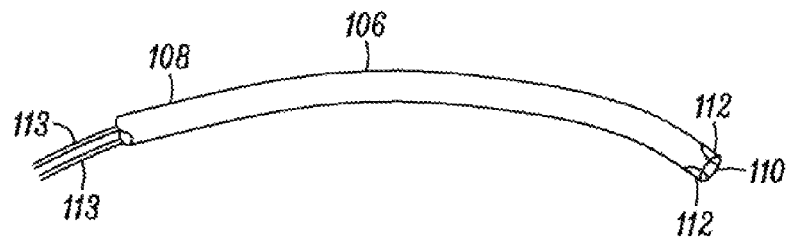
FIG. 23A is a perspective view of an alternate temporary pacing electrode for insertion into the apparatus shown in FIG. 23.
Figure 23B:
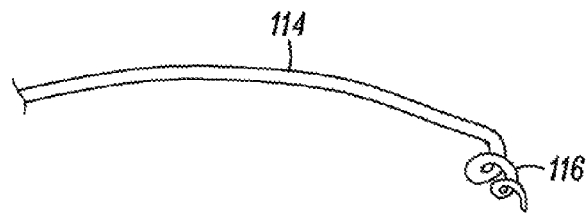
FIG. 23B is a perspective view of a lead for insertion into the apparatus shown in FIG. 23.

Turning briefly to FIGS. 23-23B another variation of the temporary pacing electrode is shown in the form of a removable conductive probe. A body 100 has a lead receiving passageway 102 extending between a distal end portion 103 and a proximal end portion 104. At the distal end portion 103, the lead receiving passageway 102 terminates in a distal outlet 105. The lead receiving passageway 102 of the body 100 may receive a removable elongated probe 106 having a proximal end 108 and a distal end 110. Temporary pacing electrodes 112 may be located on the distal end 110 of the elongated probe 106. Conductors 113 extend through the probe between the proximal and distal ends 108 and 110 for connection to a pacing signal source at the proximal end portion 104 of the body 100. The elongated probe 106 with the temporary pacing electrodes 112 is inserted into the proximal inlet of the lead receiving passageway 102 and extended along the passageway to the distal end portion 103 and through the distal outlet 105. Contact between the conductive electrode(s) and the heart surface allows pacing of the heart. After the pacing the heart with the temporary pacing electrodes to establish the desired location for lead implantation, the probe 106 may be removed from the passageway 102 so as to allow insertion of a lead 114 shown in FIG. 23B through the passageway 102. The distal end 116 of the lead will be attached to the selected lead placement site which was determined by the temporary pacing electrodes to be the suitable lead placement site.

Although the temporary pacing electrode has been particularly described and shown for used in connection with lead placement, it is contemplated that one or more temporary pacing electrodes may be used for a variety of other medical procedures including but limited to other procedures associated with the heart. For example, the temporary pacing electrode may be used to repeatedly temporarily pace the heart at a plurality of locations as necessary so as to map or analyze the conductive pathways of the heart tissue. The temporary pacing electrode may be disposed on any of the previously described apparatus of the present invention or as a separate conductive probe as described above. Other variations and uses of the temporary pacing electrodes are also possible without departing from this aspect of the present invention.

Doppler Sensor

Turning back to FIGS. 6A-6C, the Doppler sensor 80 will now be described. The Doppler sensor 80 is preferably disposed adjacent to the distal outlet 99 for the purpose of identifying whether the lead placement outlet is too close to a coronary artery. A conductive element 118 having a distal end 117 and a proximal end 119 is in communication with the Doppler sensor 80 at its distal end 117. The conductive element 118 extends to a more proximal portion of the body for communication with an operator-readable output device, which is shown generally at 120 in FIG. 7. In FIG. 6B the Doppler element 80 is positioned in the lower surface 93 of the body 92 adjacent the distal outlet 99. When the distal end portion 16 of the body 92 is put into contact with a heart surface, use of the Doppler sensor allows for detection of a coronary artery in proximity to the distal outlet 99.

The structure and function of a Doppler sensor 80 is apparent to one skilled in the art and is described in U.S. Pat. No. 4,887,606 to Yock, et al., which is incorporated herein by reference. Variations in the positioning of the Doppler sensor are possible although positions adjacent the distal outlet 99 are preferred in order to more accurately determine the proximity of the coronary to the distal outlet before attachment of the lead. It is also possible to configure the Doppler sensor 80 at the end of a removable elongated probe, similar to the removable probe previously described relative to FIGS.

23-23B, so as to allow the Doppler sensor to be removably inserted into the lead receiving passageway prior to insertion of the lead.

Expandible Member

Figure 7:
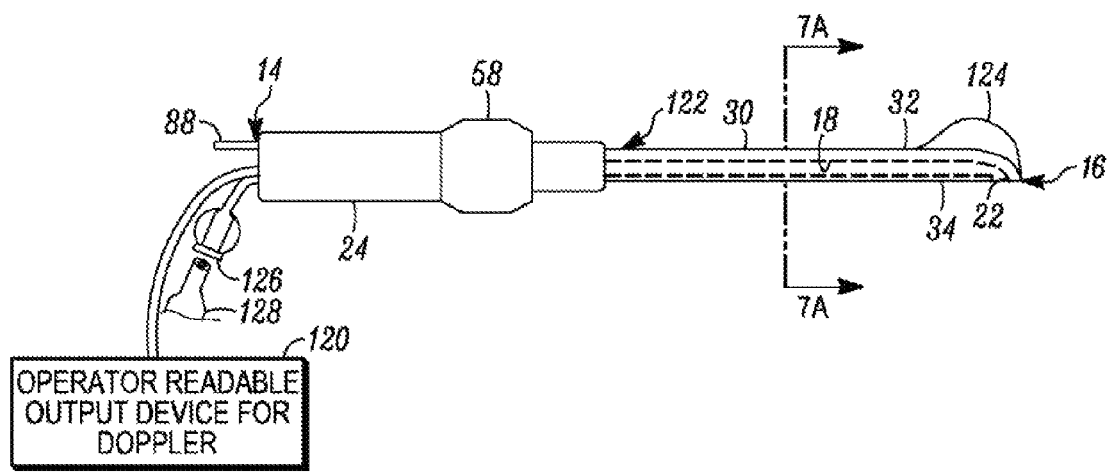
FIG. 7 is a side view of a fourth embodiment of the lead placement apparatus having an expandible member.
Figure 7A:
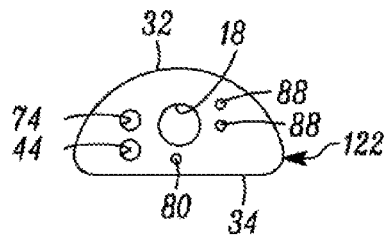
FIG. 7A is a sectional view along line 7A-7A in FIG. 7.

Now turning to FIGS. 7-10, a body, generally indicated at 122, is similar in some respects to the body of FIGS. 1-4C with like parts shown with like number. In other respects, the body 122 of FIGS. 7 and 7A is different in that it includes the inflation lumen 74, previously described, and an expandible member 124. In FIGS. 7-10 the expandible member 124 is shown as a balloon although other forms are also possible, some of which will be described below.

As shown in FIGS. 7 and 7A, the expandible member 124 is disposed in proximity to the distal outlet 22. In FIG. 7 the balloon 124 is positioned on the upper surface 32 of the body opposite the distal outlet 22. The balloon extends along the upper surface 32 of the body from the very end of the distal end portion 16 to a more proximal location along the body. It can be seen that the body, when it is inserted into a patient adjacent a cardiac surface and the balloon 124 is expanded by utilizing an inflation source, the balloon tends to bias the body 122 so that the lower surface 34 or distal outlet 22 is oriented and held adjacent the selected heart surface. The inflation lumen 74, as shown in cross section in FIG. 7A, extends along the body and communicates at its distal opening with the expandable member 124. A proximal opening 126 of the inflation lumen 74 is connected to an inflation source, indicated at 128. The inflation source is typically filled with a fluid, preferably liquid, although a variety of liquids or gases may be used as will be apparent to one skilled in the art.

In FIG. 7A the cross-sectional configuration of the body is shown as non-circular although the invention is not limited to a non-circular cross-sectional body shape and other shapes are also possible. The particular body shown in FIGS. 7 and 7A further includes temporary pacing electrodes connected to corresponding conductors 88, a Doppler sensor 80, and a vacuum lumen 44 to assist in positioning the body against the epicardial surface—although both an inflation device and a vacuum feature may not be required on the same device. These features are shown by way of example and other combination of features may be used without departing from the scope of this aspect of the invention.

Figure 8:
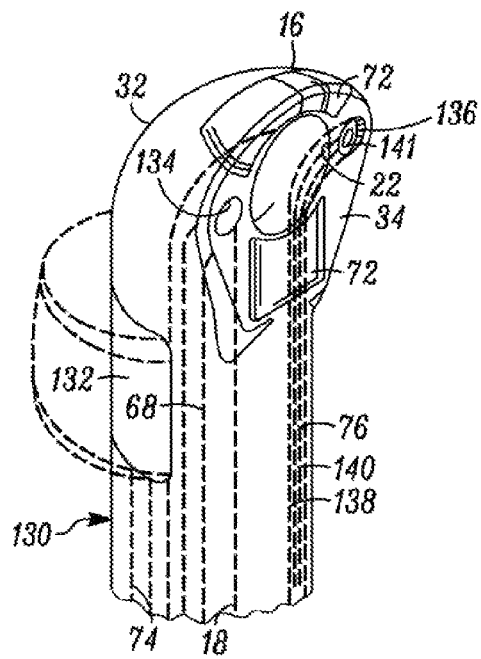
FIG. 8 is a perspective view of the distal end portion of a fifth embodiment of a lead placement apparatus having an expandible member shown in an unexpanded condition.
Figure 9:
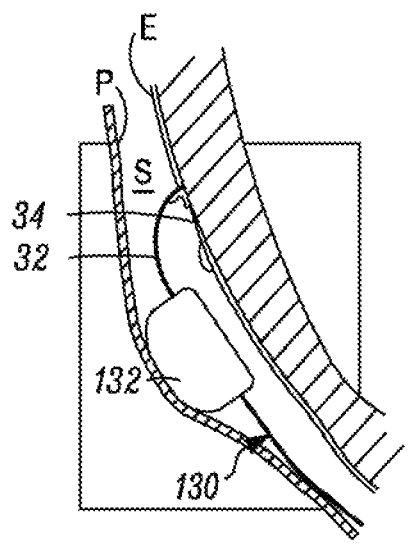
FIG. 9 is a side elevation view, illustrating the lead placement apparatus of FIG. 8 between the pericardium and epicardial surface of a heart with the expandible member shown in an expanded condition.

FIGS. 8-9 illustrate another variation of the balloon-type expandible member with like parts shown with like number. In FIG. 8, a body 130 extending between a distal end portion 16 and a proximal end portion (not shown) includes an upper surface 32 and a lower surface 34 along its length. At the distal end portion 16, a distal outlet 22 is located in the lower surface 34 and a portion of the lower surface adjacent the distal outlet 22 has a flattened shape. The expandible member 132 is located along the upper surface 32 and is spaced slightly from the distal end portion 16 of the body, although it could be directly opposite the outlet 22. FIG. 8 illustrates the unexpanded position of the balloon in solid lines, and the expanded position of the balloon as dotted lines. In the unexpanded position the balloon rests substantially against the upper surface 32 of the body to provide a generally smooth body surface and a small body profile. In the expanded position, the balloon is spaced from the upper surface of the body.

FIG. 9 shows the expanded position of the balloon when the body 130 has been inserted into the pericardial space S. The body 130 has sufficient length so as to allow insertion of the distal end portion into the pericardial space. The lower surface 34 of the body 130 in the vicinity of the distal outlet 22 is oriented towards the epicardial surface E. Once inserted, the expandible member 132 is inflated from its non-expanded to expanded position as fluid flows through the inflation lumen 74 and fills the balloon. The expanded balloon pushes against the pericardium P, thus biasing the lower surface 34 of the body 130 into contact with the epicardial surface E, the distal outlet 22 of the body being oriented in the desired direction for lead placement.

In the particular device illustrated in FIG. 8, the body further includes a dedicated guide wire lumen 68, temporary pacing electrodes 72, and the endoscope lumen 76, all of which may be used to facilitate lead placement.

The functions and construction of the various other passageways have been previously described. The endoscope lumen 76 extends through the body 130. A distal opening 136 of the endoscope lumen is located adjacent the distal outlet 22 of the lead receiving passageway 18. A proximal opening 137 of the endoscope lumen is disposed on a more proximal location of the body 130. An endoscope or fiber optic viewing device 138 which has a proximal and distal ends 140 and 142 is connected to a suitable output viewing device, such as a video monitor or the like and inserted into the proximal opening 137 of the endoscope lumen, by way of a suitable electrical or fiber optic connection. The distal end 142 of the endoscope is advanced to the distal opening 136 and allows for viewing of the selected lead placement site.

Figure 10:
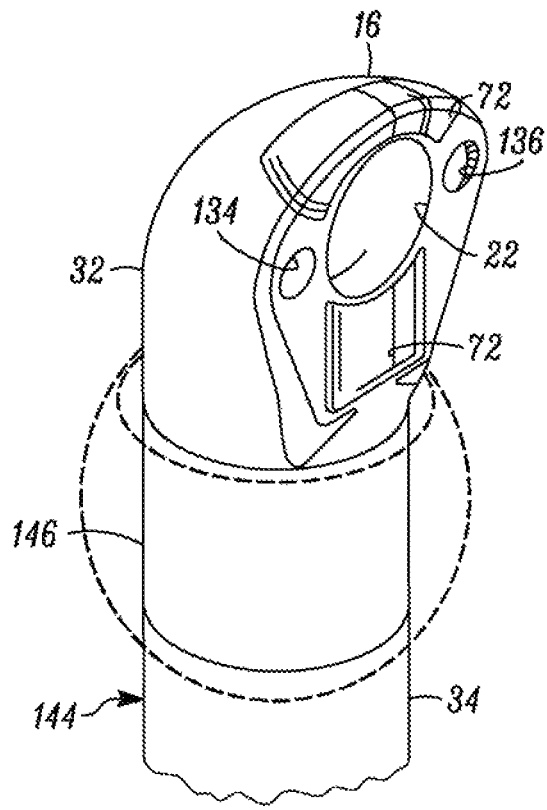
FIG. 10 is a perspective view of an alternate expandible member which extends fully circumferentially relative to the lead placement apparatus.

FIG. 10 illustrates another body 144 which is similar to the body 130 of FIGS. 8 and 9 with like parts being shown with like number, except that a balloon-type expandible member 146 extends completely around the body. In the illustrated example the expandible member 146 is spaced a small distance from the distal outlet 22 and is circumferentially disposed on the body. As the expandible member 146 is inflated to its expanded position, shown in dotted lines in FIG. 10, it expands outwardly relative to the body in a radial direction.

Figure 11:
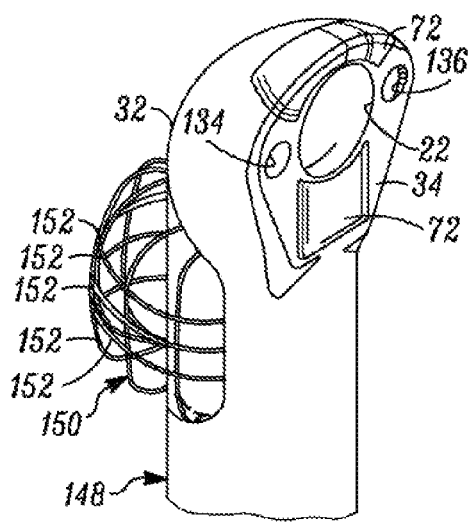
FIG. 11 is a perspective view, similar to FIG. 8, showing another type of an expandible member.
Figure 12:
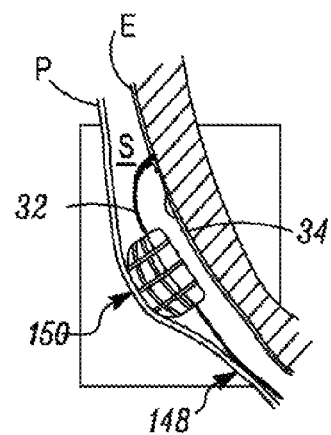
FIG. 12 is a side elevation view, similar to FIG. 9, showing the expandible member of FIG. 11 in situ between the pericardium and epicardial surface of a heart.

FIGS. 11-12 illustrate a body 148 which is similar to the one shown in FIG. 8, with like parts being shown with like numbers, except the body in FIGS. 11-12 has another type of expandible member, generally indicated at 150, which is comprised of a plurality of biasing members 152 which are longitudinally and laterally disposed relative to the body. The biasing members 152 are disposed substantially aligned with the upper surface 32 in an unexpanded condition. In an expanded position shown in FIGS. 11-12, the biasing members 152 form a cage-like structure. As shown in FIG. 12, the expanded biasing members push against the pericardium P in order to bias the lower surface 34 in the vicinity of the distal outlet 22 in contact with the epicardial surface E. The biasing members are actuated to their expanded position using a spring, release wire, or other like methods. The biasing members may be normally biased to their expanded position and held in an unexpanded position during insertion by a suitable insertion sleeve, trocar or like device. Alternately, the biasing members may be moved to the expanded position using a mechanical linkage, pull wire or the like, which is actuated from a more proximal portion of the body 150.

Figure 13:
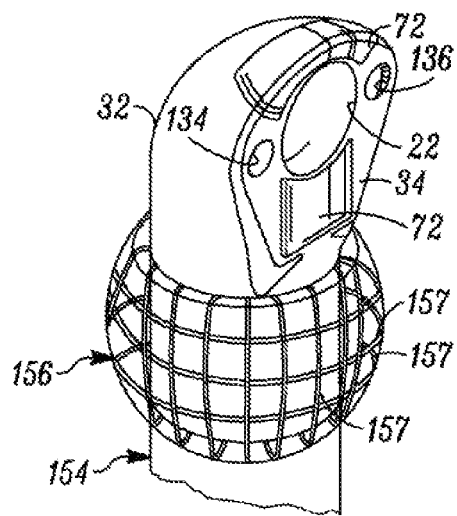
FIG. 13 is a perspective view showing a further expandible member which extends fully circumferentially relative to the lead placement apparatus.

FIG. 13 illustrates an alternate body 154 similar to the one shown in FIGS. 11-12 except that an expandible member 156 is disposed circumferentially on the distal end portion of the body and spaced a small distance from the distal outlet 22. The expandible member is comprised of biasing members 157 which are longitudinally and laterally disposed relative to the longitudinal axis of the body.

Other types of expandible members are possible in addition to the expandible members shown in FIGS. 7-13 without departing from this aspect of the present invention including but not limited to an elastomeric membrane. Also, more than one expandible member may be positioned on the body, and if needed, and these may be positioned at different locations along the body.

Method of Lead Placement

FIGS. 14-18 illustrate the method of placing a lead on a heart surface. FIG. 14 shows a patient's chest cavity, including a rib cage RC, a right lung RL, a left lung LL, a xyphoid XP, a heart HT, surrounded by a pericardium P, and percutaneous incision 158. Although the method will be shown and described by employing a preferred sub-xyphoid approach, this approach is by way of example and not limitation as other approaches may be utilized to carry out various aspects of the claimed method with departing from the present invention. FIG. 14 shows a lead placement apparatus, generally indicated at 160, which includes a body, generally indicated at 162.

In FIGS. 15-17, the body 162 may have a non-circular shape, such as a convex upper surface 164 and a convex lower surface 166, and defines a lead receiving passageway 168 terminating in a distal outlet 170. The body 162 may have a plurality of lumens or passageways to carry out a variety of functions during the lead placement procedure. As shown by way of example but not limitation, these lumen or passageways may include a guide wire lumen 172 terminating at a guide wire outlet 174, temporary pacing electrodes 176 disposed adjacent the distal outlet 170 and connected by way of conductors 178 through the body to a pacing signal source, an endoscope lumen 180, and a steering member 182.

Turning back to FIGS. 14-14D the incision 158 through the patient's skin is made in the vicinity of the xyphoid XP. Then the guiding or trocar apparatus 160 is inserted through the percutaneous incision 158 to the pericardium P. Access to the pericardial space S as defined between the pericardium P and the epicardial surface E is made using an appropriate dilator device, indicated generally at 184, which slices, punctures or otherwise gains access to the pericardial space through the pericardium. These devices will be apparent to one skilled in the art and may include but are not limited to needles, cutting tools, guide wires, dilators, and other devices. It is noted that the incision 158 is approximately 3 mm to 5 mm in length and is made in the area of the xyphoid and the costal cartilage CC. A device such as a needle, or the like, may then be advanced through the incision 158 toward the heart. A viewing device may be used to aid the advancement of the needle. Access can be made into the pericardium employing known techniques, which by way of example but not limitation these techniques can include a fluoroscopic contrast injection. A thin guide wire, indicated generally at 186, such as, for example, a 0.018 inch thickness guide wire is then advanced under fluoroscopic guidance into the pericardial space. Successively thicker guide wires can be inserted and removed sequentially into the pericardial space in order to sufficiently widen the incision for entry of the body 162. The sizes of these guide wires will vary. Examples of successively larger guide wires can range approximately between 0.018-0.05 inch and preferred sizes include 0.035 or 0.038 inch. An introduction sheath, or dilator, indicated generally at 188, may be introduced over the guide wire into the pericardial space. FIGS. 14A-14D sequentially illustrate the introduction of the needle 184, the guide wire 186, the dilator 188, and insertion of the lead placement apparatus 160 through the dilator 188.

FIGS. 15 and 16 illustrate insertion of the body 162 into the pericardial space S between the pericardium P and the epicardial surface E. The body is inserted into the pericardial space S a distance of approximately between 20 cm and 30 cm. If the body has a non-circular cross-sectional shape, such shape may extend along all or a portion of the body which is inserted into the pericardial space.

As can be seen in FIG. 16, the distal outlet 170 is defined in the lower surface 166 of the body 162 so that when the body is inserted into the pericardial space the distal outlet 170 is oriented adjacent the epicardial surface E for lead placement.

In FIG. 15 a guide wire 189 having a distal end 190 and a proximal end 191 is inserted into the guide wire lumen 172 and extends forwardly of the guide wire outlet 174. Prior to lead placement, the guide wire 189 may be used to assist in locating the desired lead placement site such as for example bisecting tissue to create a clear path for lead placement. The body 162 is moved within the pericardial space until the distal outlet 170 is positioned at a selected lead placement site. Movement of the distal outlet 170 may be effectuated by the steering wire 182 where force is applied to the steering member at the proximal end portion of the body. An endoscope or other viewing device may be inserted into the endoscope lumen 180 so as to allow viewing of the epicardial surface as well as the selected lead placement site.

Prior to lead placement the heart is preferably paced utilizing at least one temporary pacing electrode 176 positioned adjacent the distal outlet 170. Pacing of the heart is performed by placing the electrodes 176 in contact with the surface of the heart at a selected location so as to determine whether the selection location is suitable for lead placement. Electrical impulses are supplied to the heart through the temporary pacing electrodes and the effect of the such impulses are transmitted to external viewing devices so as to determine the optimal lead placement site.

Although the use and function of the temporary pacing electrode has been particularly described in connection with lead placement, it is contemplated that the temporary pacing electrode may be used in connection with a variety of other diagnostic and/or therapeutic medical procedures such as, for example, for mapping and analyzing the conductive pathways of the heart. The temporary pacing electrode may be inserted into the pericardial space either as part of any of the previously described apparatus or a separate pacing apparatus. The temporary pacing electrode may be used repeatedly or sequentially at various locations so as to map and/or analyze the various conductive pathways of the patient's heart.

FIG. 16 illustrates a lead 192 having a distal end 194 and a more proximal end 196. The lead is inserted into the lead receiving passageway 168. Once the selected lead placement site has been identified, the distal end 194 of the lead 192 is advanced through the distal outlet 170 for attachment or engagement to the epicardial surface E. The lead 192 engages either the epicardial surface E or the endocardial surface, located beneath the epicardial surface or both. The distal end 194 of the lead preferably has an anchor that secures it to the heart surface. The anchor may take any of several well known forms, such as barb or a curved and pointed end which may be in the form of a screw or helix so as to facilitate attachment. Other shapes will be apparent so as to secure the lead to the heart and different shapes may be appropriate depending on the degree of lead permanence required. The steps of lead placement may be repeated so as to engage a plurality of leads with a surface of the heart.

Figure 18:
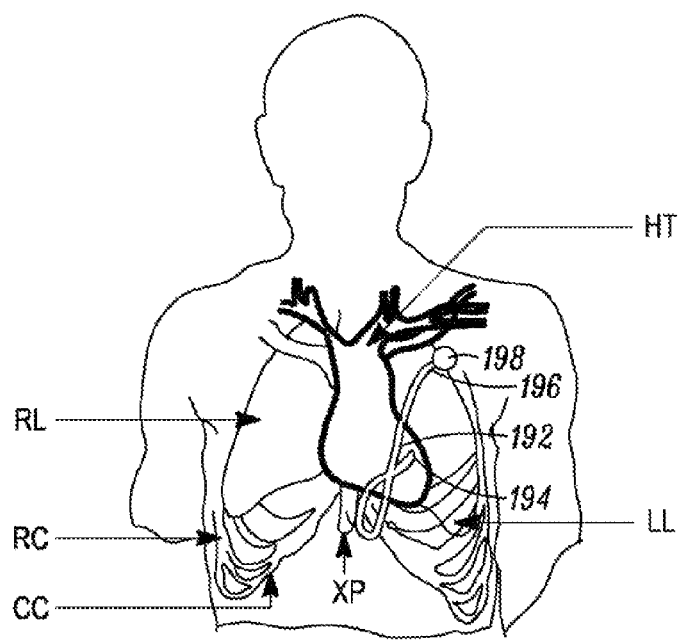
FIG. 18 is an anterior plan view of the patient's heart which shows implantation of a lead and connection of the lead to a pacer signal source.

FIG. 18 shows the patient's chest after lead placement has occurred. The lead placement apparatus is withdrawn from the patient's chest. A portable pacer source 198 may implanted into the subclavicular space, preferably the left subclavicular space, so as to provide an electrical pacing signal to the lead 192 by way of a connection between the proximal end 196 of the lead and the pacer source 198.

The method has been shown by way of example but not limitation using the above steps. It is realized however that other variations for performing the method of lead implantation are also possible and may be utilized in place of or in addition to the steps of the method already described. For example, the method may be performed utilizing a body having a vacuum lumen describe above relative to FIGS. 3-4C or FIGS. 6A-6C. A vacuum source provides suction to hold the distal outlet against the surface of the heart. In addition, the method of lead placement utilizing the temporary pacing electrodes is not limited to a body having a non-circular shape.

A method of lead placement includes providing a body having the Doppler sensor 80, as shown and described relative to FIGS. 6A-6C, or a separate Doppler sensor. After the body is introduced into the pericardial space, the Doppler sensor is placed in contact with the epicardial surface at a selected location. As discussed relative to FIGS. 6A-6C, the Doppler sensor is located in the lower surface of the body although other positions are possible. Once in contact with the heart surface, the Doppler sensor is activated to detect whether the sensor or distal outlet 22 is in proximity to a coronary artery of the heart. The information is transmitted along the conductive element to the Doppler output device where it is read by the operator. If a coronary artery is detected, the body is moved to another lead placement site. Successive detecting is performed so as to avoid placement of the lead in proximity to a coronary artery. If no coronary artery is detected unduly close to the distal outlet, the lead is advanced from the distal outlet and engaged with one or both of the epicardial and endocardial surfaces of the heart in a similar manner as shown in FIG. 16. Thereafter, the lead placement apparatus may be withdrawn. Although the method may be performed where at least a portion of the body has a non-circular shape, the method of lead placement which includes the Doppler sensor is not limited to a body having a non-circular shape.

As shown and described in FIGS. 7-13, the expandible member is deployed from an unexpanded position to an expanded position, such as by an inflation source or movement of biasing members. The expandible member is carried by the body and disposed in the vicinity of the distal outlet so as to hold or bias the distal outlet against the selected lead placement site. Amongst the steering members, vacuum lumen and expandible member, any one or a combination thereof may be utilized so as to orient the distal outlet against a selected lead placement site.

The method of lead placement further may include the introduction of a fluid to the heart surface, in which event the body has a fluid delivery lumen as described in relation to FIG. 5E.

Lead Removal

The present invention contemplates a variety of techniques or body designs that facilitate removal of the lead from the body after implantation. FIGS. 25-41A are directed to a body construction and lead arrangement which facilitate removal of the lead from the lead placement apparatus and, in particular, in which the lead is removed from the lead placement apparatus in a direction which is transverse to the longitudinal axis of the body. Transverse lead removal as described below may be incorporated into any one or more previously described aspects of the invention.

Figure 25:
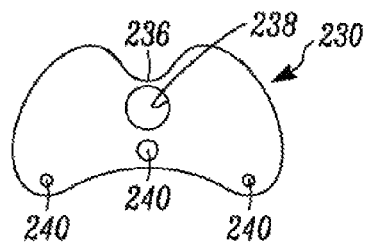
FIG. 25 is an enlarged transverse sectional view of a tenth embodiment of the lead placement apparatus which is adapted to allow removal of a lead in a direction transverse to the longitudinal axis of the apparatus.
Figure 26:
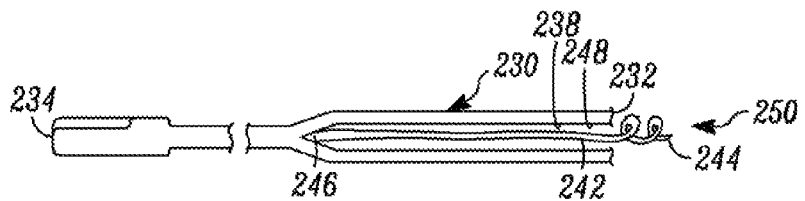
FIG. 26 is a longitudinal sectional view of the apparatus of FIG. 25 including a lead.

FIGS. 25 and 26 illustrate a body 230 having a distal end portion 232 and a proximal end portion 234. Although the body is shown having a non-circular shape in the transverse direction along at least a portion of the body, other shapes may also be employed.

In FIG. 25, the body, generally indicated at 230, includes a longitudinally extending seam or thin wall portion 236, a lead receiving passageway 238 and passageways 240. The thin wall portion 236 is so called because it is thinner relative to the remaining portions of the body and it is adjacent to or forms a portion of the inner surface of the lead receiving passageway. The thin wall portion 236 extends from a distal end portion 232 of the body to a more proximal portion of the body, and may extend to the proximal end portion 234 of the body or any intermediate body position. The thin wall portion 236 preferably extends at least along the portion of the body which is inserted into the pericardial space of a patient. Where a sub-xyphoid approach is employed, the length of the thin wall portion 236 may range approximately between 10 cm and 40 cm, preferably 20 cm to 30 cm. A lead 240 having a distal end 244 and a more proximal end 246 is shown inserted into the lead receiving passageway 232 during the lead placement procedure.

In the embodiment of FIG. 26, the lead 242 is removed from the body by separating the body along the thin wall portion 236. The thin wall portion may be thin enough or may even be perforated along its length so as to facilitate separation. Such separation may be initiated at the distal end portion 232 of the body or along a more proximal portion and then separation extends axially in an "unzipping" manner, from the initial separation site. By way of example but not limitation, FIG. 26 shows separation of the thin wall portion extending from the distal end portion 232 and extending proximally to create a longitudinally disposed opening along the body. Thereafter, the lead 242 may be removed from the body in a transverse direction to longitudinal axis 250 of the body. Although the body is shown-having a plurality of passageways 240 which may incorporate any combination of features previously described to facilitate lead placement, these passageway are not intended to limit the present invention.

Figure 27:
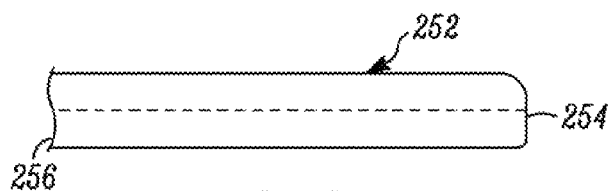
FIG. 27 is a side view of an eleventh embodiment of the lead placement apparatus which allows lead removal in a transverse direction to the longitudinal axis of the apparatus.
Figure 28:
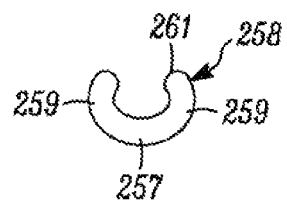
FIG. 28 is an end vie w of the embodiment shown in FIG. 27.

FIGS. 27 and 28 illustrate an alternative body, generally indicated at 252, having a distal end portion 254 and a proximal end portion 256 and defining a longitudinally disposed channel, generally indicated at 258, which extends in a proximal direction from the distal end portion 254. The channel is approximately C-shaped or U-shaped, and has a bottom wall 257 and side walls 259. The channel has a top opening 261 to allow for lead removal. The channel 258 is adapted to receive a lead which is removed through the top opening 261 in a direction which is transverse to the longitudinal direction of the body. The channel 258 may extend along the entire length of the body or any portion of the body. More specifically, the width of the top opening 261 in the channel is preferably smaller than the diameter of the lead 242, to normally retain the lead within the channel. The body is preferably made of resilient polymeric material so that the side walls 259 flex outwardly to allow the top opening 261 to widen for removal of the lead.

Figure 29:
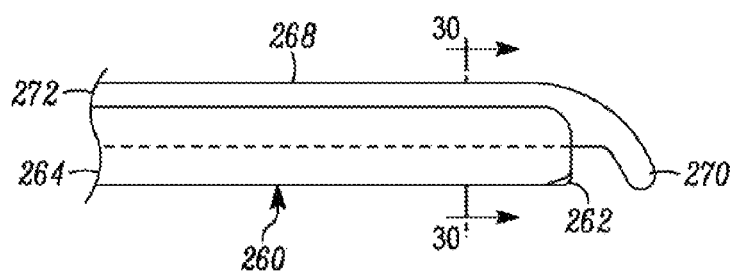
FIG. 29 is a side view of a twelfth embodiment of the lead placement apparatus which allows removal of the lead in a transverse direction to the longitudinal axis of the apparatus.
Figure 30:
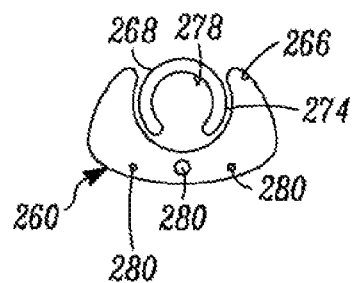
FIG. 30 is a sectional view along line 30-30 of FIG. 29.

FIGS. 29 and 30 illustrate lead removal in accordance with another aspect of the invention. A body, generally indicated at 260, has a distal end portion 262 and a proximal end portion 264 and defines a channel 266 which is similar to the channel described in previous FIGS. 27 and 28 having a bottom wall, sides walls and an top opening except that the body 260 in FIGS. 29 and 30 includes an elongated C-shaped portion 268 which is received within the channel 266. The C-shaped portion 268 has a distal end 270 and a proximal end 272 and, when assembled with the channel, captures the lead between them.

Viewed in the transverse direction, as shown in FIG. 30, the C-shaped portion 268 is located within the channel 266, and has an outer convex surface 274 that cooperates with the inner concave surface of the channel 266 and is sized slightly smaller than the channel 266 so as to be received therein. The assembly of the C-shaped portion 268 and the channel 266 defines a lead receiving passageway 278 for insertion of the lead. The body 260 may have a non-circular shape in the transverse direction although other shapes are possible. A plurality of passageways 280 also may be defined within the body and utilized to incorporate the features previously described. The C-shaped portion 268 may be slidably or rotatably received within the channel 266. In this embodiment, the lead may be released in two different ways. First, the C-shaped portion 268 may be rotated within channel 266 until the gaps or slots are aligned, allowing the lead to be removed from the body. Alternatively, the C-shaped portion 268 and channel 266 may be peeled apart, revealing the lead located therebetween.

Figure 40:
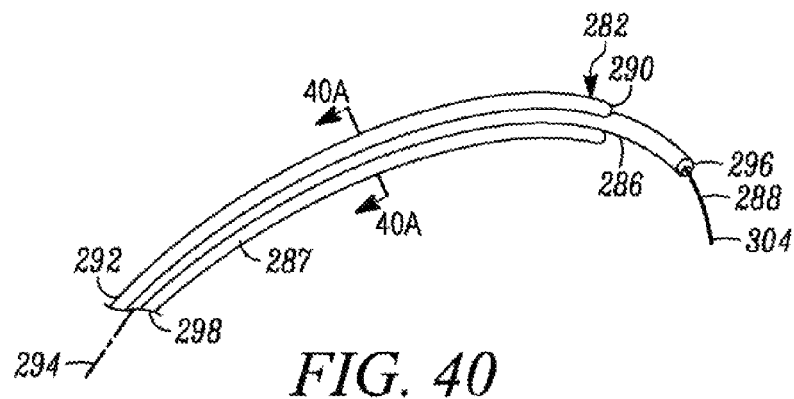
FIG. 40 is a side view of a seventeenth embodiment of the lead placement apparatus which allows removal of the lead in a transverse direction to the longitudinal axis of the apparatus.
Figure 41:
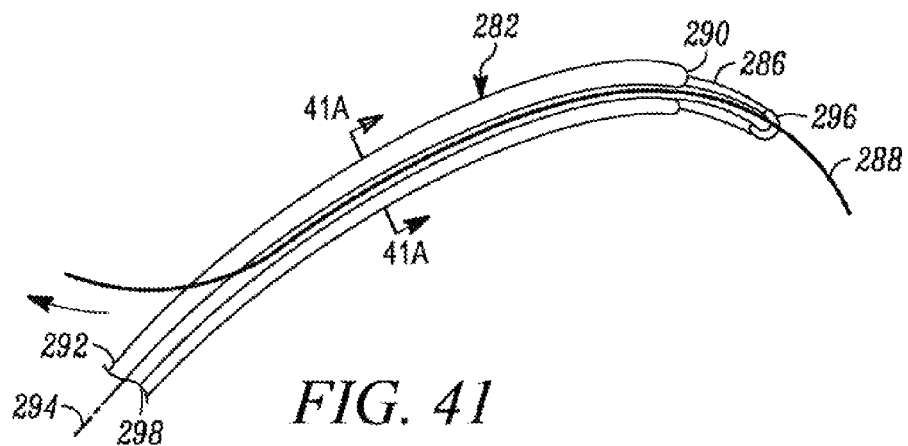
FIG. 41 is a side view of the apparatus of FIG. 40 in an open position.
Figure 41A:
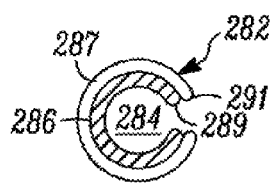
FIG. 41A is a sectional view of along line 41A-41A of FIG. 41.

FIGS. 40-41A employ a similar arrangement, and generally illustrate rotational movement of a longitudinally disposed portion relative to the remainder of the body. A body, generally indicated at 282, defines a lead receiving passageway 284 and has a circular shape in the transverse direction. The body is comprised of inner and outer longitudinally disposed portions 286 and 287, respectively, which are concentrically positioned relative to one another and together define the lead receiving passageway 284 which receives a lead 288. At least one of the longitudinally disposed portions is rotated relative to the other. Each inner and outer portion 286 and 287 has an opening 289 and 291, respectively, which extends longitudinally along each portion. Although each opening may vary in size and may vary relative to one another, the size of each opening is larger than the thickness of the lead so as to allow for lead removal transverse to the longitudinal axis of the body when the openings are aligned.

Figure 40A:
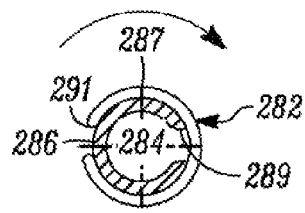
FIG. 40A is a sectional view along line 40A-40A of FIG. 40.

In FIGS. 40A and 41A, the outer longitudinally disposed portion 287 extends between a distal end portion 290 and a proximal end portion 292 and defines a longitudinal axis 294. The inner longitudinally disposed portion 286 is received within the lead receiving passageway 284 and extends between a distal end 296 and a proximal end 298. In FIGS. 40 and 41, at least one of the inner and outer portions may be curved at an acute angle relative to a longitudinal axis 294 of the body although other angles of curvature between 10 degrees and 80 degrees are possible. For example, one of the inner and outer shaft may be curved and the other may be straight in a similar manner as described relative to FIGS. 19-20. The longitudinal position of inner and outer portions 286 and 297 may be fixed relative to one another or capable of relatively slidable movement.

FIGS. 40 and 40A illustrate a first position of the body 282 where the openings 289 and 291 are circumferentially non-aligned relative to one another. The lead 288 is inserted into the passageway 284 and a distal end 300 of the lead may be advanced past the distal ends 290 and 296 of both longitudinally-disposed portions. Removal of the lead may be achieved by rotating at least one of the inner and outer portions 286 and 287 relative to one another to a second or opened position, as shown in FIGS. 41 and 41A, in which the openings 289 and 291 are in circumferential alignment with one another. FIGS. 40A and 41A illustrate rotational movement of the outer longitudinally disposed portion 287 relative to the inner longitudinally disposed portion 286 in the direction indicated by the arrow in FIG. 40A. Removal of the lead is illustrated by the arrow in FIG. 41.

Turning back to FIGS. 31-32B, they illustrate another lead placement apparatus having a body, generally indicated at 302, which defines a longitudinal axis 304 and a lead receiving passageway 306, and includes distal and proximal end portions 308 and 310, respectively, and a longitudinally disposed seam indicated generally at 312. The body 306 is designed to separate along the longitudinally disposed seam 312 for lead removal in a transverse direction. The seam 312 is defined by interlocking longitudinal edges of the body. One of the longitudinal edges includes a projection 314 and the other longitudinal end includes a recess 316 so that when the body defines a closed position as shown in FIG. 32A the projection 314 is seated within the recess 316.

Figure 32A:
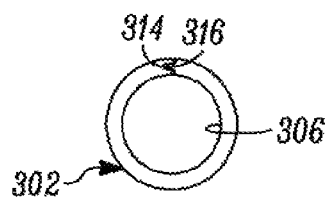
FIGS. 32A-32B are end views of the embodiment shown in FIG. 31 showing closed and open positions, respectively.
Figure 32B:
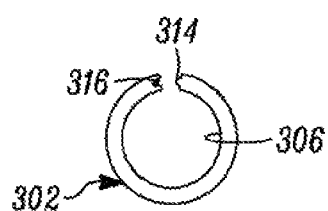

Removal of the lead 318 is achieved by separating the seam at one or both of the distal or proximal end portions 308 and 310. The body is made of any suitable material or combination of materials which imparts flexibility characteristics. Examples of materials include, but are not limited to, polymeric material, common in medical devices. The material may have shape retention characteristics such as by thermoforming or the like, so that the body normally defines a closed position (as seen in FIG. 32A but without the need for interlocking features), but spreads apart easily as seen in FIG. 32B. Alternately, a malleable metal strip may be disposed within the body of FIG. 32A and surrounded by a non-metal material which maintains a normally closed position. Force applied to the metal strip may separate the projection 314 from the recess 316. Although the shape of the body 306 is shown as circular, other shapes, such as the non-circular shapes described above, are also possible without departing from this aspect of the present invention.

Figure 31:
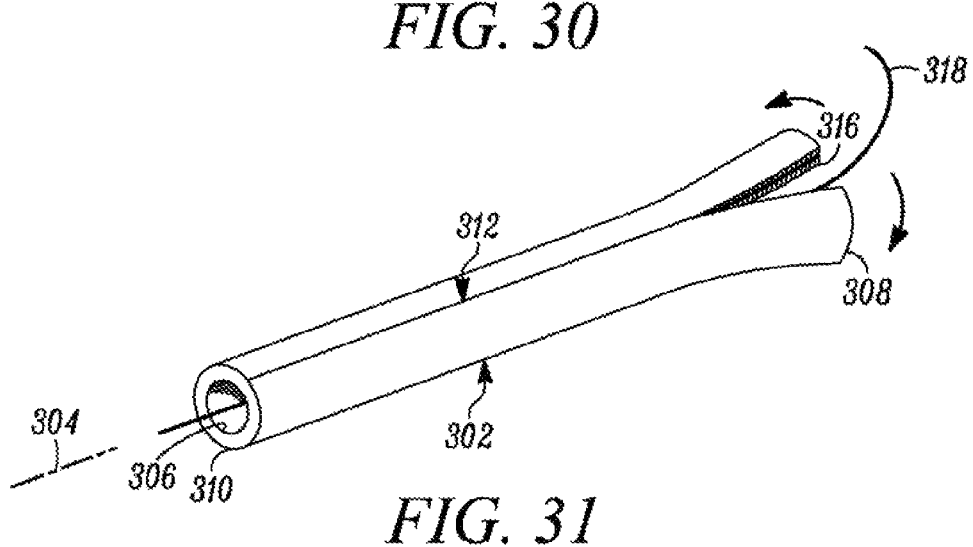
FIG. 31 is a perspective view of a thirteenth embodiment of the lead placement apparatus which allows removal of the lead in a transverse direction to the longitudinal axis of the apparatus.
Figure 33:
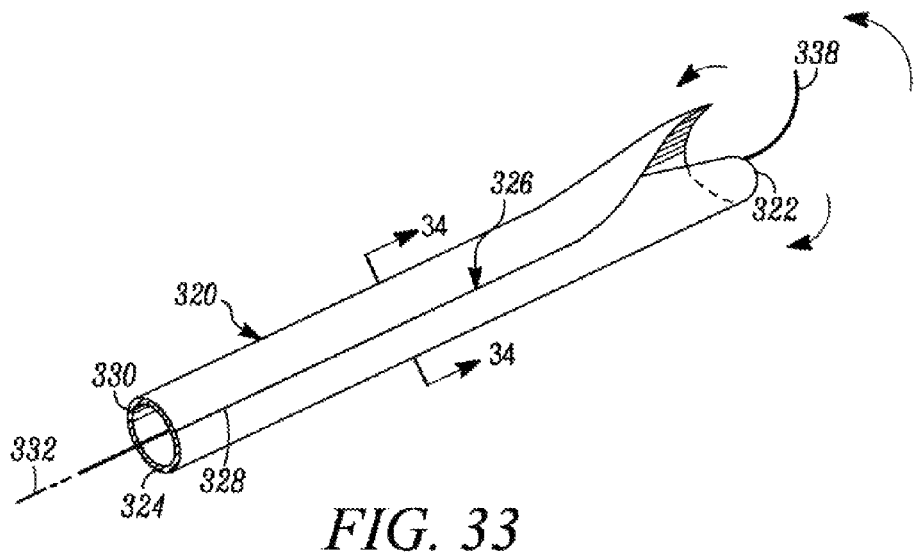
FIG. 33 is a perspective view of a fourteenth embodiment of the lead placement apparatus which allows removal of the lead in a transverse direction to the longitudinal axis of the apparatus.
Figure 34:
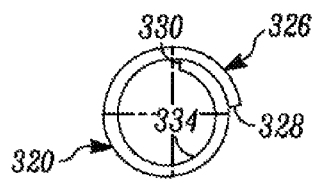
FIG. 34 is a sectional view along line 34-34 in FIG. 33.

In FIGS. 33 and 34, an alternate body, indicated generally at 320, is shown having distal and proximal end portions 322 and 324, respectively, and including a seam indicated generally at 326, which is similar to the body in FIGS. 31-32B, except that the seam is closed by overlapping longitudinal edges 328 and 330, respectively, along of the body 320. The seam 326 is axially spaced from a longitudinal axis of the body 332. A lead 338 received within the passageway 334 may be removed in a transverse direction, by temporarily spreading the overlapping edges to form a longitudinal gap through which the lead maybe withdrawn as indicated in FIG. 33.

Figure 35:
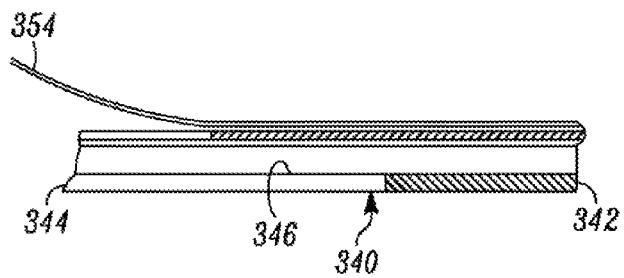
FIG. 35 is a longitudinal sectional view of a fifteenth embodiment of the lead placement apparatus which allows removal of the lead in a transverse direction to the longitudinal axis of the apparatus.
Figure 36:
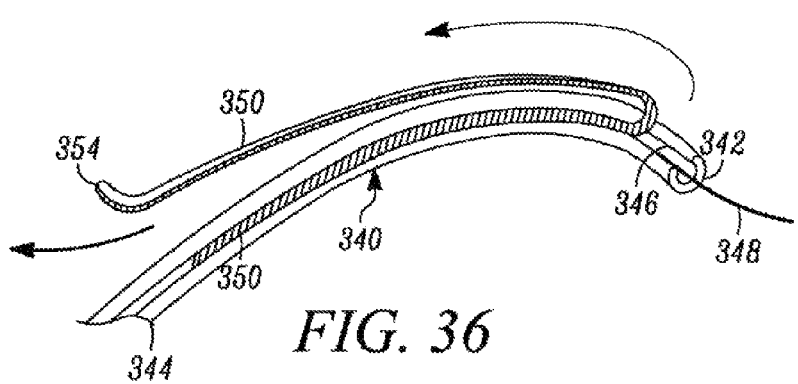
FIG. 36 is a side view of the embodiment shown in FIG. 35 showing removal of a longitudinally disposed portion of the apparatus.
Figure 37:
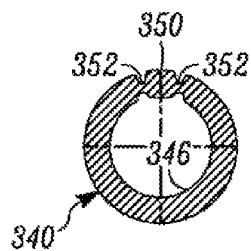
FIG. 37 is a partial transverse sectional view of the embodiment shown in FIGS. 35-36.

FIGS. 35-37 illustrate a yet further embodiment of the lead placement apparatus which allows for removal of the lead in a transverse direction. A body, generally indicated at 340, includes distal and proximal end portions 342 and 344, respectively, and defines a lead receiving passageway 346 extending between the distal and proximal end portions for receiving a lead 348. The body includes a longitudinally disposed weakened portion 350 which is bounded between two thin walled portions or other lines of weakness 352. A separate filament or wire is connected to the distal end of the weakened portion 350, or an extension of the portion 350 extends in a proximal direction terminating at a tab 354 which is disposed in a more proximal portion of the body. As illustrated in FIG. 36, removal of the lead 148 from the body 340 may be achieved by pulling proximally on the tab 354 (or pulling on the wire or filament), as indicated by the arrow, causing separation along the thin walled portions 352, thus opening the passageway 346 so as to allow removal of the lead in a transverse direction.

Figure 38:
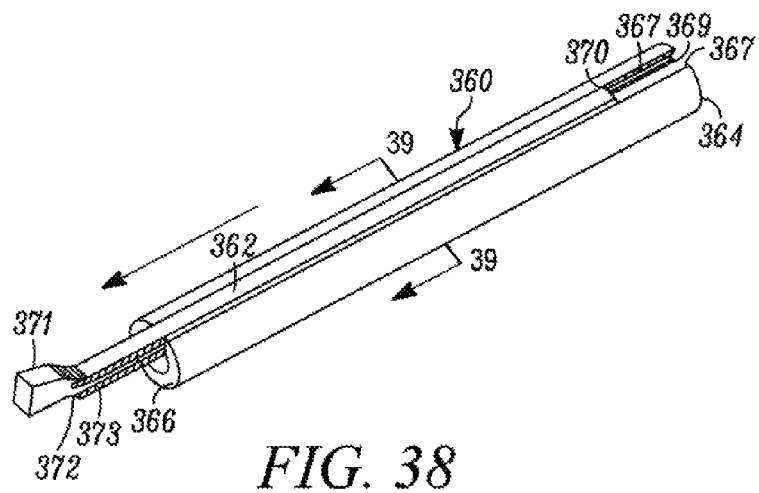
FIG. 38 is a perspective view of a sixteenth embodiment of the lead placement apparatus which allows removal of the lead in a transverse direction to the longitudinal axis of the apparatus.
Figure 39:
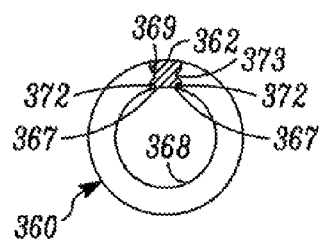
FIG. 39 is a section view along line 39-39 of FIG. 38.

In FIGS. 38 and 39 an alternate body, generally indicated at 360, is shown similar to the body shown in FIGS. 35-37, except that the body 360 includes a longitudinally disposed slide 362 which is slidably moveable relative to the remaining portion of the body in order to allow lead removal in a transverse direction. The body 360 includes distal and proximal end portions 364 and 366, respectively and defines a passageway 368 for receiving a lead. In the transverse direction shown in FIG. 39 the body may have a circular or other shape and include a longitudinal opening between two longitudinally disposed edges 367 extending around the circumference of the body. The opening is defined along the body between the distal and proximal end portions 364 and 366. Each longitudinal edge 367 may include a projection 369 which also extends along the body and into side slots or recesses 373 of the slide member 362.

As shown in FIG. 38, when the slide is slidably moved in a proximal direction as indicated by the arrow, the opening defined between the longitudinal edges 369 is unobstructed and permits lead removal in a direction which is transverse relative to the body.

Epicardial Lead

Figure 42:
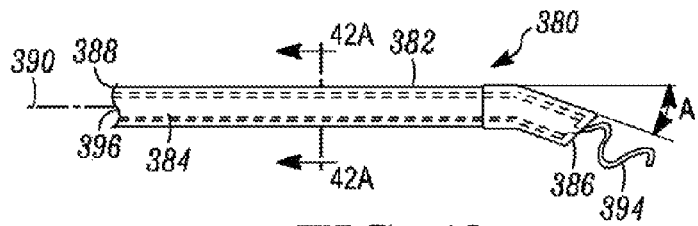
FIG. 42 is a side view of an epicardial lead having an angled distal end portion.
Figure 42A:
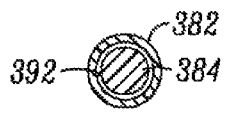
FIG. 42A is a sectional view along line 42A-42A of FIG. 42.

FIGS. 42 and 42A illustrate an epicardial lead, generally indicated at 380, which is comprised of an elongated outer sheath 382 and an inner member 384. The outer sheath 382 is made of an insulated material whereas the inner member is conductive. The sheath 382 includes a distal end portion 386 and a proximal end portion 388 and defines a longitudinal axis 390 therebetween. The outer sheath 382 is hollow and is preferably, but not exclusively, cylindrical in cross-sectional shape. A passageway 392 is defined by an inner surface of the outer sheath 382 for receiving the inner member 384.

As best seen in FIG. 42, the distal end 386 of the sheath 382 is fixed at an acute angle A relative to the longitudinal axis 390. By way of example but not limitation, the angle A is approximately 20 degrees relative to the longitudinal axis. It is realized that other acute angles may be utilized, such as between 10 degrees and 80 degrees, although the preferred range of the angle is between approximately 30 degrees to 60 degrees for directing a contact member toward the surface or the heart. The length of the angled portion of the sheath itself may measure approximately 10 mm to 20 mm.

As shown in FIG. 42, the inner member 384 has a distal section 394 and a proximal section 396. As with the sheath 382, the inner member 384 is elongated relative to the longitudinal axis 390 and generally defines a cylindrical cross-sectional shape. At the distal section 394, the inner member 384 defines a contact anchor, which may be in the form of a nonlinear shape, preferably but not exclusively in the form of a helical or screw-like shape, so as to facilitate attachment of the inner member 384 to the epicardial surface of the heart. FIG. 42A shows the inner member 384 as having a solid cylindrical cross-section, although other configurations and shapes are also possible without departing from the present invention. The inner member is preferably made of a flexible or malleable material and comprises one or more conductive elements or wires which may be connected to a pacing signal source at the proximal section 396.

In FIG. 42A the sheath 382 and the inner member 384 are capable of movement relative to one another so as to implant the inner conductive member on the epicardial surface of the heart. For example, the inner member 384 is moved so as to move the distal section 394 of the inner member distally of the distal end portion 386 of the outer sheath 382. Any relative movement may be utilized, such as rotational, translational or a combination thereof. In addition, the epicardial lead can be configured to allow movement of the inner member in a direction which is transverse to the longitudinal axis 390 in accordance with previously described aspects of the invention.

When lead implantation is desired, relative movement between the inner member and the outer sheath causes the distal section 394 of the inner member to be moved through the fixed angle A at the distal end portion 386. As the distal section 394 passes through the distal end portion 386, it assumes the angled position relative to the longitudinal axis 390. Continued relative movement moves the distal section 394 beyond of the distal end portion 386 for contact with the heart of a patient and, in particular, the epicardial surface. The distal section 394 allows for attachment of the inner member to the epicardial surface of the heart in any conventional manner, without the need for attachment from an orthogonal direction as found in prior art leads. For example, the helical shape of the distal section may be implanted or embedded into the epicardial surface of the heart by simple rotational movement of the inner conductive member.

Figure 51:
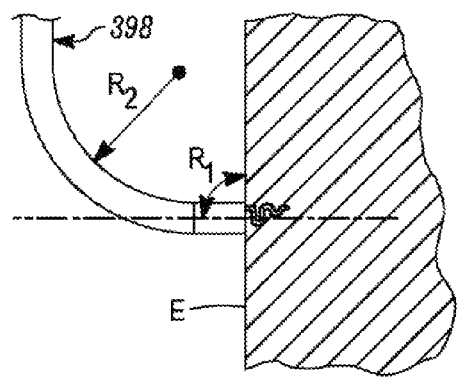
FIG. 51 is a side elevation view of a prior art epicardial lead placing the lead on a surface of the heart.
Figure 52:
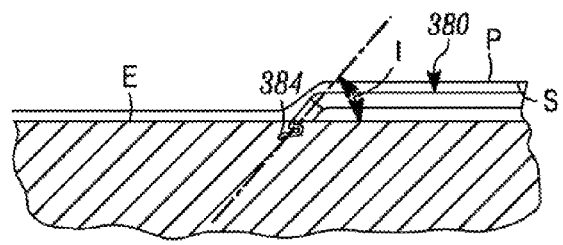
FIG. 52 is a side elevation view of the epicardial lead of the present invention placing the lead on a surface of the heart.
Figure 53:
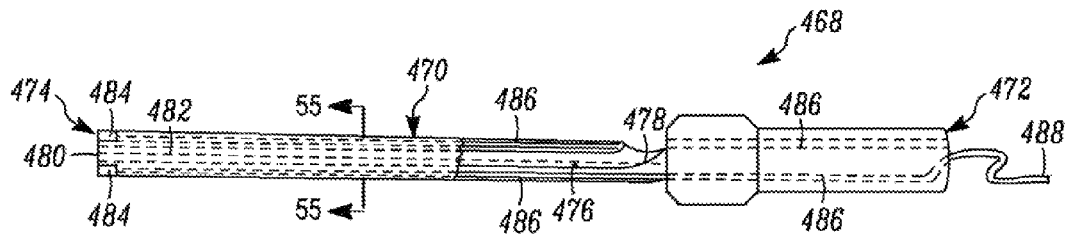
FIG. 53 a side view of a further embodiment of a lead placement apparatus of the present invention with portions of the apparatus shown in section.
Figure 54:
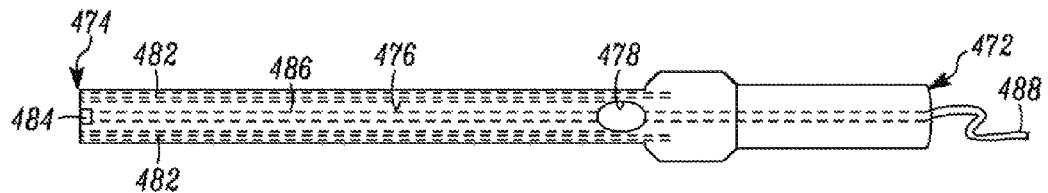
FIG. 54 is a plan view of the lead placement apparatus of FIG. 53.
Figure 55:
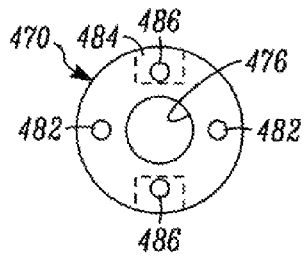
FIG. 55 is a sectional view along line 55-55 of FIG. 53.
Figure 56:
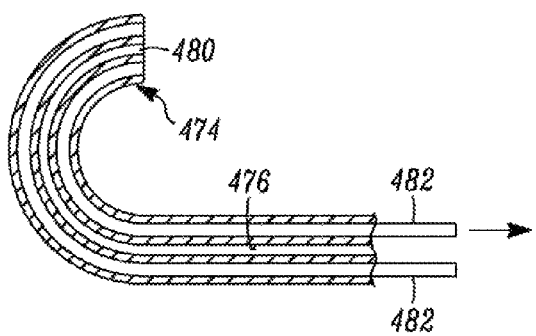
FIG. 56 is an enlarged partial longitudinal sectional view of the lead placement apparatus of FIG. 53 with the distal end portion shown in a deflected configuration.

Turning briefly to FIG. 51-52, FIG. 52 generally illustrates attachment of the inner member 384 of the epicardial lead 380 to the epicardial surface E of the heart where the distal section is disposed at an acute angle 1, which ranges approximately between 10 degrees and 80 degrees, preferably between 30 degrees and 60 degrees. By contrast, FIG. 51 shows an epicardial lead, generally indicated at 398, found within the prior art. The epicardial lead requires the distal end to be disposed at a right angle R1 so that the distal end is perpendicular to the epicardial surface and thus the epicardial lead forms a 90 degree bend relative to radius indicated at R2.

Figure 43:
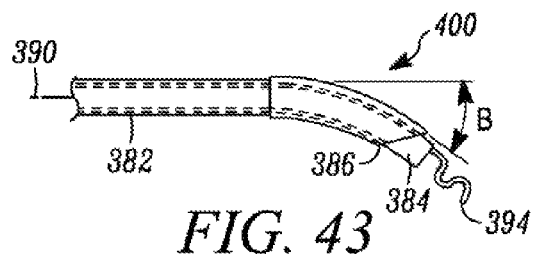
FIG. 43 is a side view of another epicardial lead having a curved distal end portion.

FIG. 43 illustrates an epicardial lead 400 similar to the one shown in FIGS. 42 and 42A, with like parts being shown with like number, except that an outer sheath 382 of the lead 400 has a distal end portion 386 which is fixed into a curved shape relative to the longitudinal axis. The angle, indicated at B, defined by the distal end portion 386 is preferably in the range approximately between 10 degrees and 80 degrees, preferably 30 degrees and 60 degrees. The length of the curved portion of the sheath measures approximately 10 mm to 20 mm.

Figure 44:
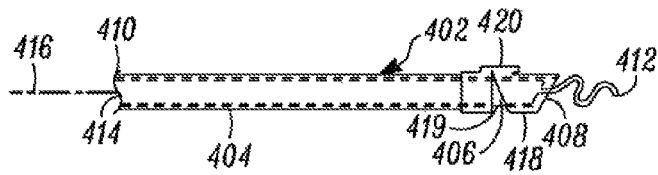
FIGS. 44-45 are side views of an epicardial lead having a distal end portion which is adapted to move between straight and angled positions, respectively.
Figure 45:
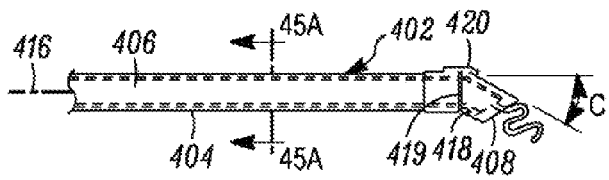
Figure 45A:
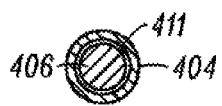
FIG. 45A is a sectional view along line 45A-45A of FIG. 45.

FIGS. 44-45A illustrate an epicardial lead, generally at 402, which is comprised of an elongated, hollow outer insulated sheath 404 and an inner conductive member 406. The sheath 404 includes distal and proximal end portions 408 and 410, respectively. Likewise, the inner member 406 includes distal and proximal sections 412 and 414, respectively. The outer sheath 404 defines a passageway 411 for receiving the inner member 406 and a longitudinal axis 416. As previously described, the outer sheath 404 and the inner member 406 are movable relative to one another.

Adjacent the distal end portion 408 of the outer sheath 404, the sheath includes a collar 418 having a sloped proximal edge 419. As shown in FIG. 44, the proximal edge slopes downwardly in a distal direction to define a gap with the remaining portion of the sheath. Along an upper surface of the sheath, the proximal edge of the collar is pivotally connected at a hinge 420 to the remaining portion of the sheath 404.

As shown in FIGS. 44 and 45, the distal end portion 408 of the sheath 404 is adapted to move between at least two positions. A first position is illustrated in FIG. 44. The distal end portion 408 is positioned so that the passageway 411 for receiving the inner member 406 is in alignment with the longitudinal axis 416. Along the lower surface of the sheath, the sloped proximal edge 419 is spaced from the remaining portion of the sheath. A second position is illustrated in FIG. 45 where the distal end portion 408 is disposed at an angle, indicated at C, relative to the longitudinal axis 416 so that the passageway is disposed at the angle C relative to the longitudinal axis.

Movement of the distal end portion is preferably controlled by a pre-set thermo-formed position of the distal end, or by a biasing member such as a spring or the like. The distal end portion is preferably biased such that the normal position of the spring results in the second position of the distal end portion shown in FIG. 45. Alternatively, control structures may be carried at the proximal end portion 410 for controlling the angular position of the distal end portion. Other control members may be used to vary the angular orientation of the distal end portion 408 apart from the angular positions shown and described above without departing from this aspect of the present invention.

Figure 46:
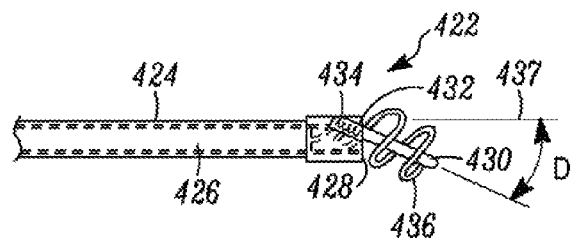
FIGS. 46-47 are side views of other epicardial leads having an angled distal end portion.

Numerous variations are also possible so as to permit attachment of the inner member to the epicardial surface of the heart at an acute angle. In FIG. 46, an epicardial lead, generally at 422, includes an outer sheath 424 and an inner member 426. A distal end portion 428 of the outer sheath carries a sensor 430 such as, for example, a pacing electrode, Doppler sensor, fiber optic viewing device or endoscope which is connected to viewing means at a more proximal portion of the epicardial lead 422. The distal end portion 428 further defines a lumen 432 extending into the sheath in a proximal direction. The lumen 432 is disposed at an acute angle relative to the longitudinal axis of the body and receives the sensor 430 therein. A spring or other biasing member 434 is disposed within the lumen so as to normally bias the sensor 430 in an extended position, illustrated in FIG. 46. Extension and retraction of the sensor may also be controlled at a more proximal portion of the epicardial lead.

In FIG. 46, a distal section 436 of the inner member 426 is preformed at an angle D relative to the longitudinal axis while the sheath 426 is aligned relative to a longitudinal axis 437. So when the distal section 436 extends distally of the sheath 424, the distal section will form the acute angle D relative to the longitudinal axis. The distal section is made of any suitable material which allows it to resume a normally curved position relative to the longitudinal axis of the lead.

Figure 47:
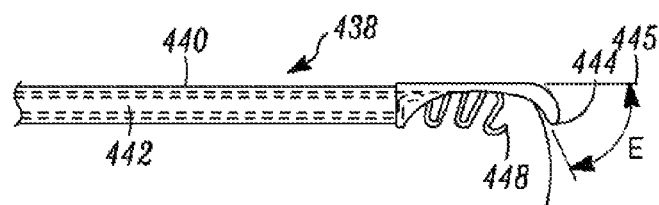

FIG. 47 illustrates another epicardial lead, generally at 438, having an outer sheath 440 and an inner member 442. A distal end portion 444 of the sheath 440 is curved at an acute angle, indicated at E, relative to the longitudinal axis 445 of the lead. The distal end portion 444 includes a transverse opening 446 relative to the longitudinal axis 445. A distal section 448 of the inner member 442 is moved through the sheath 440 and extends through the transverse opening 446. The transverse opening 446 has a convex inner surface, so that when the distal section 448 of the inner member 442 is advanced, the distal section engages the convex inner surface of the opening 446 so as to be disposed at the angle E relative to the longitudinal axis.

Figure 48:
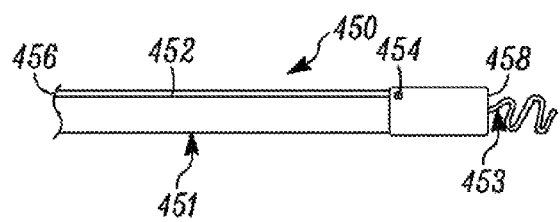
FIG. 48 is a side view of another epicardial lead having a distal end portion which is adapted to move between straight and angled positions.

In FIG. 48 an epicardial lead, generally at 450, which generally includes an outer sheath 451 and an inner member 453, includes a steering member 452, such as a pull wire, having a distal end 454 and a proximal end 456. The distal end 454 of the steering member is connected in the vicinity of a distal end portion 458 of the sheath 451. So the distal end portion 458 is moved upon application of force to the steering member at the proximal end 456. Tensile compressive or rotational force may be applied to the steering members so as to move the distal end portion in a desired direction for lead placement.

Figure 49:
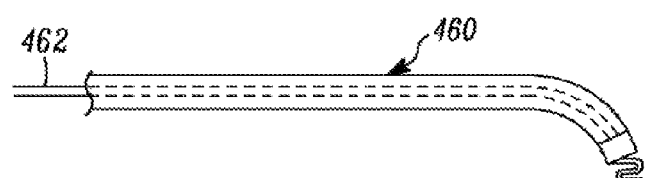
FIG. 49 is a side view of an epicardial lead including a steering member.

In FIG. 49, an alternate epicardial lead, generally at 60, utilizes a malleable elongated wire 462 which may be shaped to retain a desired angular orientation for lead placement. The wire 462 is similar to that previously described in relation to FIG. 24. Other features may also be utilized to facilitate lead placement in accordance with previously discussed features.

Figure 50:
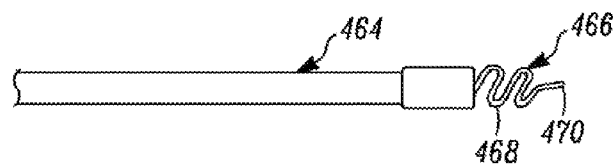
FIG. 50 is a side view of an epicardial lead having an alternate distal section.

FIG. 50 shows an epicardial lead 464 having a distal section, generally at 466, with an alternate shape. The distal section 466 has a nonlinear portion 468 as well as a linear portion 470. The linear portion is distally located relative to the nonlinear portion and is used like a guide wire which may be used to dissect cardiac tissue and facilitate lead placement. Many other shapes and orientations are possible are possible without departing from this aspect of the present invention.

FIGS. 53-62 illustrate additional variations in the lead placement apparatus and method of the present invention. In FIGS. 53-56 a lead placement apparatus generally indicated at 468 includes an elongated body generally at 470. The body 470 defines a longitudinal axis and generally includes a proximal end portion 472 and a distal end portion 474. As shown particularly in FIG. 55, the body is illustrated having a circular cross sectional shape although other shapes are also possible. A lead receiving passageway 476 is defined within the body extending between a proximal inlet 478 and a distal outlet 480. The passageway 476 generally is shown as a centrally located lumen within the body although other positions are possible. One or more steering members 482 are disposed within the body and are adapted to deflect the distal end portion 474 of the body from, for example, a straight configuration shown in FIG. 54 to a curved configuration shown in FIG. 56, when force is applied to at least one of the steering members in the direction indicated by the arrow. The body 470 also may include at least one temporary pacing electrode 484 and associated conductive element(s) 486 which connect to a pacing signal source at a distal end 488, preferably outside of the patient's body.

As shown in FIGS. 53-56, the body is suitably flexible so as to allow deflection of the distal end portion 474 upon application of force to the steering members. The body also has sufficient stiffness so as to allow for rotational movement of the body during the lead placement procedure. The body can be rotated up to 360 degrees relative to its longitudinal axis. It is also possible that a portion of the body may be rotated relative to the remaining portion of the body, for example, the portion of the body extending into the pericardial space may be adapted for rotation up to 360 relative to the handle or proximal end portion 472 of the body. Because the tip is deflectable in at least one plane and the body has torsional rigidity that allows it to be rotated, the tip can, in effect, be deflected up to 360 degrees.

Figure 57:
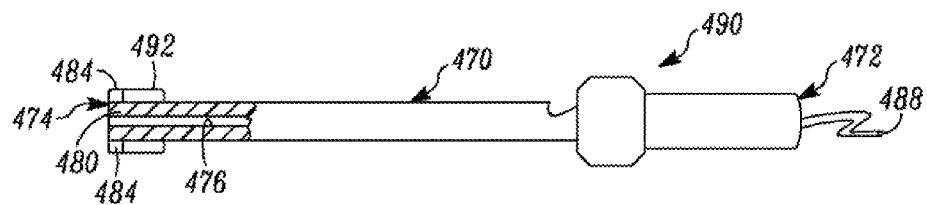
FIG. 57 is a side view of a still further embodiment of a lead placement apparatus having an expandible member with the distal end portion shown in section.
Figure 58:
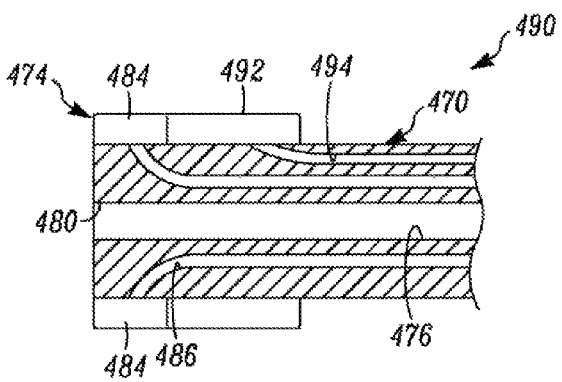
FIG. 58 is an enlarged partial longitudinal sectional view of the distal end portion of the lead placement apparatus in FIG. 57.
Figure 59:
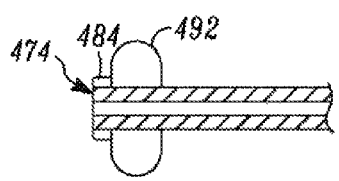
FIG. 59 is a partial longitudinal sectional view of the lead placement apparatus in FIG. 57 showing the expandible member in an enlarged configuration.

FIGS. 57-59 illustrate an alternate lead placement apparatus 490 which is similar to the apparatus 468 in FIGS. 53-56, with like parts being shown with like number, except that the apparatus of FIGS. 57-59 includes an annular expandible member 492, preferably a balloon type expandible member, which is carried by the body 470. As shown in FIG. 58, an inflation lumen 494 is disposed within the body 470 and is in fluid communication with an inflation source generally at the proximal end portion 472 of the body. FIG. 59 illustrates selective expansion of the balloon.

Figure 60:
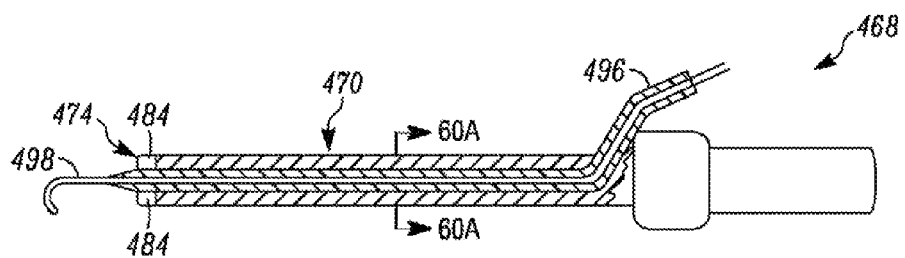
FIG. 60 is a side view of the lead placement apparatus in FIG. 53 with portions of the apparatus shown in section showing insertion of a guiding or trocar device.
Figure 60A:
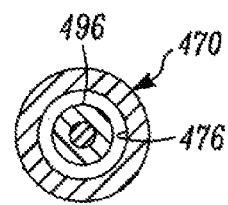
FIG. 60A is a cross sectional view along line 60A-60A in FIG. 60.
Figure 61:
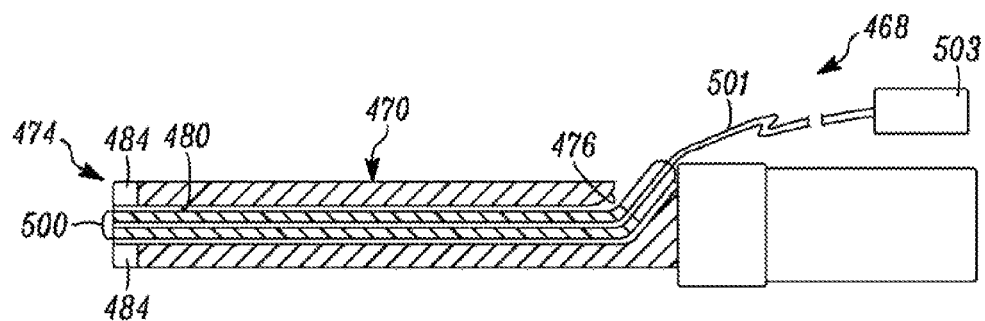
FIG. 61 is a side view of the lead placement apparatus, similar to FIG. 60, showing insertion of a Doppler sensor.

In FIGS. 60-60A a guiding or trocar device 496 is illustrated and insertably received within the lead receiving passageway 476. It is contemplated that the lead receiving passageway is suitably sized for temporarily receiving devices in addition to a lead during the lead placement procedure. These devices are preferably, but not necessarily, removed from the lead receiving passageway prior to insertion of the lead. A guide wire 498 is insertably received within the trocar device 496 and can be advanced beyond the distal end portion 474 of the body 470 so as to help locate the selected lead placement site. As shown in FIG. 61, a Doppler sensor 500 is generally disposed in proximity to the distal outlet 480 and is connected through a conductor 501 to an operator readable output device 503. The Doppler sensor 500 may be configured as part of a sensing device which is inserted into the lead receiving passageway 476 and advanced through the body 470 to the distal outlet 480 for sensing the proximity of the distal outlet to a coronary artery. Alternatively, the Doppler sensor can be mounted to the distal end portion 474 of the body in proximity to the distal outlet 480.

Figure 62:
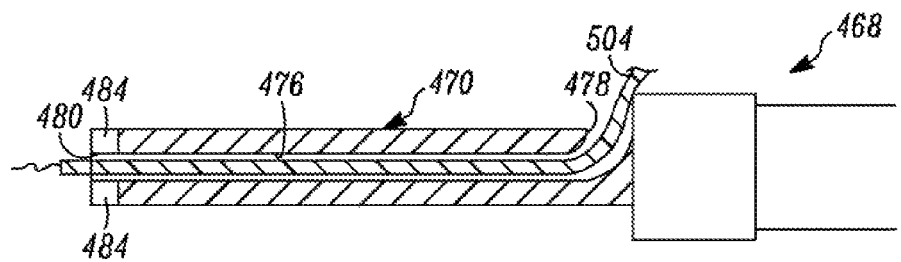
FIG. 62 is a side view of the lead placement apparatus, similar to FIG. 60, showing insertion of a lead.

FIGS. 60-62 also illustrate a method which utilizes the lead placement apparatus of FIGS. 53-56. In FIG. 60 the trocar 496 and guide wire 498 are inserted into the lead receiving passageway 476 and through the body 470 so as to facilitate introduction of the body into the pericardial space. A distal portion of the guide wire 498 may extend beyond the distal end portion 474 of the body 470. The guide wire 498 may assist in piercing the pericardium or, alternatively, piercing of the pericardium may be performed separately by another appropriate instrument, for example, a needle or other like devices. Thereafter the guide wire and/or the trocar 496 may be inserted into the pericardial space to dilate the initial incision and widen the incision so as to allow insertion of the distal end portion 474 of the body 470 into the pericardial space. The guide wire and trocar are removed from the lead receiving passageway 476 and, if necessary, additional guide wires, dilators or other introduction sleeves of larger diameter may be inserted into the lead receiving passageway 476 so as to suitably widen the incision for introducing the body 470 into the pericardial space. Once the distal end portion 474 of the body has been introduced into the pericardial space, the distal outlet 480 may be oriented in the desired direction for lead placement using the steering members 482. At least a portion of the body may also be rotated in 360 degrees. The temporary pacing electrodes 484 may be placed in contact with successive locations of the epicardial surface of the heart for pacing of the heart.

FIG. 61 illustrates insertion of the Doppler sensor 500 into the lead receiving passageway 476. The Doppler sensor 500 and its associated sensing device are inserted into the body to detect whether the selected lead placement site is in proximity to a coronary artery. If a coronary artery is detected, then the distal end portion is moved so as to avoid placement of the lead on a coronary artery. For example, the distal end portion 474 may be deflected using the steering members or it may be rotated, as necessary. The Doppler sensor is preferably removed prior to lead placement.

In FIG. 62, a lead 504 is inserted into the lead placement device 468 at the proximal inlet 478 and advanced to the distal outlet 480. The lead is engaged with the selected lead placement site. A suitable retention member may be disposed at the distal end of the lead for attachment to the epicardial or endocardial surface of the heart. Once lead placement is completed, the lead placement apparatus may be withdrawn.

The lead placement apparatus may be utilized to perform the method in a similar manner as described relative to the lead placement apparatus of FIGS. 53-56. The expandable member can be enlarged after the distal end portion of the apparatus has been inserted into the pericardial space so as to enlarge the existing working and viewing space at the distal end portion of the body.

Accordingly, apparatuses and methods for placing a lead on a surface of the heart has been provided that meets all the objects of the present invention. While the invention has been described in terms of certain preferred embodiments, there is no intent to limit the invention to the same. Instead it is to be defined by the scope of the appended claims.

We claim:

1. An apparatus for placing a lead at a target site on an epicardial surface of a heart using a minimally-invasive delivery procedure, the epicardial surface of the heart having a convex shape and being surrounded by a pericardial sac, an inner surface of the pericardial sac conforming to the epicardial surface and defining a concave shape, the apparatus comprising:

an elongated body including a proximal end portion and a distal end portion and defining a lead receiving passageway extending between a proximal inlet and a distal outlet for receiving a lead therethrough for contact with the surface of the heart, wherein the distal end portion includes a distal end of the elongated body, the distal end portion having a non-circular portion extending along at least a part of the distal end portion and the distal end portion defining a contact surface configured to contact and conform to the epicardial surface, wherein the non-circular portion has a non-circular axial cross-sectional shape, the non-circular portion gradually tapering in a distal direction from a proximal end of the non-circular portion to the distal end of the elongated body such that the distal end portion forms a tapered leading end that is adapted to facilitate advancement of the distal end portion through a pericardial space located between the convex epicardial surface and the concave pericardial inner surface, wherein the distal outlet is defined entirely in the non-circular portion, and wherein the distal end portion includes an expandable member configured to bias the distal outlet against the epicardial surface;

at least one steering member extending through the elongated body from the distal end portion to a more proximal portion of the body, the steering member being adapted to move the distal end portion of the body in at least one plane when force is applied to the steering member at the proximal end portion the body; and a steering collar accessible to a user and axially spaced from the distal end portion of the body and concentrically and circumferentially supported around the proximal end portion of the body, the collar being in operative engagement with the at least one steering member and adapted so that movement of the steering collar causes movement of the distal end portion.

2. The apparatus of claim 1 wherein the elongated body is adapted to place the lead on an epicardial surface of the heart.

3. The apparatus of claim 1 wherein the steering member is adapted to move the distal end portion of the body when tensile force is applied to the steering member.

4. The apparatus of claim 1 wherein the steering member is adapted to move the distal end portion of the body when compressive force is applied to the steering member.

5. The apparatus of claim 1 wherein the steering member is adapted to move the distal end portion of the body when torsional force is applied to the steering member.

6. The apparatus of claim 1 wherein the steering member includes one or more elongate elements.

7. The apparatus of claim 1 wherein the steering member includes a plurality of wires.

8. The apparatus of claim 1 wherein the steering member is adapted to move the distal end portion of the body in at least two planes.

9. The apparatus of claim 1 wherein the elongated body defines a longitudinal axis and at least the distal end portion of the body is curved relative to the longitudinal axis.

10. The apparatus of claim 9 wherein the steering member is adapted to move the distal end portion of the body from a curved position to a less curved position.

11. The apparatus of claim 9 wherein the steering member is adapted to move the distal end portion of the body so as to increase the relative curvature of at least the distal end portion of the body relative to the longitudinal axis.

12. The apparatus of claim 1 wherein at least the distal end portion of, the body is curved relative to the longitudinal axis in at least one plane in the range of approximately 10 degrees to 80 degrees.

13. An apparatus for placing a lead at a target site on an epicardial surface of a heart using a minimally-invasive delivery procedure, the epicardial surface of the heart having a convex shape and being surrounded by a pericardial sac, an inner surface of the pericardial sac conforming to the epicardial surface and defining a concave shape, the apparatus comprising:

an elongated body including a proximal end portion and a distal end portion and defining a lead receiving passageway extending between a proximal inlet and a distal outlet for receiving a lead therethrough for contact with the surface of the heart, the distal end portion including a non-circular portion of the body having a non-circular axial cross-section, the non-circular portion tapering distally from a proximal end to a distal end of the non-circular portion and being adapted to retain a body orientation between the inner surface of the pericardial sac and the epicardial surface, wherein the distal outlet is defined entirely in the non-circular portion, and wherein the distal end portion includes an expandable member configured to bias the distal outlet against the epicardial surface;

at least one steering member extending through the elongated body from the distal end portion to a more proximal portion of the body, the steering member being adapted to move the distal end portion of the body in at least one plane when force is applied to the steering member at the proximal end portion the body; and a steering collar accessible to a user and axially spaced from the distal end portion of the body and concentrically and circumferentially supported around the proximal end portion of the body, the collar being in operative engagement with the at least one steering member and adapted so that movement of the steering collar causes movement of the distal end portion.

14. The apparatus of claim 13 wherein the steering member is adapted to move the distal end portion of the body when tensile force is applied to the steering member.

15. The apparatus of claim 13 wherein the steering member is adapted to move the distal end portion of the body when compressive force is applied to the steering member.

16. The apparatus of claim 13 wherein the steering member includes a plurality of wires.

17. The apparatus of claim 13 wherein the steering member is adapted to move the distal end portion of the body in at least two planes.

18. The apparatus of claim 13 wherein the elongated body defines a longitudinal axis and at least the distal end portion of the body is curved relative to the longitudinal axis.

* * * * *